US010435662B1

(12) United States Patent
Masquelier et al.

(10) Patent No.: US 10,435,662 B1
(45) Date of Patent: Oct. 8, 2019

(54) AUTOMATED CONTROL OF CELL GROWTH RATES FOR INDUCTION AND TRANSFORMATION

(71) Applicant: Inscripta, Inc., Boulder, CO (US)

(72) Inventors: Don Masquelier, Boulder, CO (US); Phillip Belgrader, Pleasanton, CA (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 16/360,404

(22) Filed: Mar. 21, 2019

Related U.S. Application Data

(60) Provisional application No. 62/649,731, filed on Mar. 29, 2018, provisional application No. 62/671,385, filed on May 14, 2018.

(51) Int. Cl.
*C12M 1/42* (2006.01)
*C12N 15/87* (2006.01)
*C12M 1/00* (2006.01)

(52) U.S. Cl.
CPC ............ *C12M 35/04* (2013.01); *C12M 29/10* (2013.01); *C12M 35/02* (2013.01); *C12M 35/08* (2013.01); *C12N 15/87* (2013.01)

(58) Field of Classification Search
CPC ....... C12M 27/10; C12M 27/20; C12M 41/36
See application file for complete search history.

(56) References Cited

U.S. PATENT DOCUMENTS

| | | | |
|---|---|---|---|
| 4,833,080 A | 5/1989 | Brent et al. | |
| 4,959,317 A | 9/1990 | Sauer et al. | |
| 5,464,764 A | 11/1995 | Capecchi et al. | |
| 5,487,992 A | 1/1996 | Capecchi et al. | |
| 5,627,059 A | 5/1997 | Capecchi et al. | |
| 5,631,153 A | 5/1997 | Capecchi et al. | |
| 5,654,182 A | 8/1997 | Wahl et al. | |
| 5,677,177 A | 10/1997 | Wahl et al. | |
| 5,885,836 A | 3/1999 | Wahl et al. | |
| 5,888,732 A | 3/1999 | Hartley et al. | |
| 6,074,605 A | 6/2000 | Meserol et al. | |

(Continued)

FOREIGN PATENT DOCUMENTS

| | | |
|---|---|---|
| CN | 22397122 Y | 9/2000 |
| EP | 2240238 | 10/2010 |

(Continued)

OTHER PUBLICATIONS

International Search Report and Written Opinion for International Application No. PCT/US2018/53608, dated Dec. 13, 2018, p. 1-9.

(Continued)

*Primary Examiner* — William H. Beisner
(74) *Attorney, Agent, or Firm* — Sarah Brashears; Dianna L. DeVore

(57) ABSTRACT

The present disclosure relates to methods and devices for automated control of cell growth rates where cell growth is measured in situ and the devices can be used as a stand-alone device or as a module in an automated environment, e.g., as one module in a multi-station or multi-module cell processing environment. The cell growth device comprises a temperature-controlled vial, a motor assembly to spin the vial, a spectrophotometer for measuring, e.g., OD of the cells in the vial, and a processor to accept input from a user and control the growth rate of the cells.

20 Claims, 22 Drawing Sheets

(56) References Cited

U.S. PATENT DOCUMENTS

| | | | |
|---|---|---|---|
| 6,143,527 A | 11/2000 | Pachuk et al. |
| 6,150,148 A | 11/2000 | Nanda et al. |
| 6,204,061 B1 | 3/2001 | Capecchi et al. |
| 6,277,608 B1 | 8/2001 | Hartley et al. |
| 6,482,619 B1 | 11/2002 | Rubinsky et al. |
| 6,509,156 B1 | 1/2003 | Stewart et al. |
| 6,654,636 B1 | 11/2003 | Dev et al. |
| 6,689,610 B1 | 2/2004 | Capecchi et al. |
| 6,746,441 B1 | 6/2004 | Hofmann et al. |
| 6,774,279 B2 | 8/2004 | Dymecki |
| 6,916,632 B2 | 7/2005 | Chesnut et al. |
| 6,956,146 B2 | 10/2005 | Wahl et al. |
| 7,029,916 B2 | 4/2006 | Dzekunov et al. |
| 7,112,715 B2 | 9/2006 | Chambon et al. |
| 7,141,425 B2 | 11/2006 | Dzekunov et al. |
| 7,422,889 B2 | 9/2008 | Sauer et al. |
| 8,110,122 B2 | 2/2012 | Alburty et al. |
| 8,110,360 B2 | 2/2012 | Serber et al. |
| 8,153,432 B2 | 4/2012 | Church et al. |
| 8,332,160 B1 | 12/2012 | Platt et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang et al. |
| 8,726,744 B2 | 5/2014 | Alburty et al. |
| 8,758,623 B1 | 6/2014 | Alburty et al. |
| 8,921,332 B2 | 12/2014 | Choulika et al. |
| 8,932,850 B2 | 1/2015 | Chang et al. |
| 9,029,109 B2 | 5/2015 | Hur et al. |
| D731,634 S | 6/2015 | Page et al. |
| 9,063,136 B2 | 6/2015 | Talebpour et al. |
| 9,316,577 B1* | 4/2016 | Doggett ............ G01N 15/0205 |
| 9,361,427 B2 | 6/2016 | Hillson |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,017,760 B2 | 7/2018 | Gill et al. |
| 2003/0059945 A1 | 3/2003 | Dzekunov et al. |
| 2003/0073238 A1 | 4/2003 | Dzekunov et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2006/0001865 A1* | 1/2006 | Bellalou ............ G01N 35/0099 356/246 |
| 2006/0224192 A1 | 10/2006 | Dimmer et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0055790 A1 | 3/2010 | Simon |
| 2010/0076057 A1 | 3/2010 | Sontheimer et al. |
| 2011/0009807 A1 | 1/2011 | Kjeken et al. |
| 2011/0065171 A1 | 3/2011 | Dzekunov et al. |
| 2011/0213288 A1 | 9/2011 | Choi et al. |
| 2011/0236962 A1 | 9/2011 | Loebbert et al. |
| 2012/0156786 A1 | 6/2012 | Bebee |
| 2013/0005025 A1 | 1/2013 | Church et al. |
| 2013/0196441 A1 | 8/2013 | Rubinsky et al. |
| 2014/0121728 A1 | 5/2014 | Dhillon et al. |
| 2014/0350456 A1 | 11/2014 | Caccia |
| 2015/0132827 A1* | 5/2015 | Simoes ............ C12N 1/20 435/252.1 |
| 2015/0191719 A1 | 7/2015 | Hudson et al. |
| 2015/0297887 A1 | 10/2015 | Dhillon et al. |
| 2016/0272961 A1 | 9/2016 | Lee |
| 2016/0281047 A1 | 9/2016 | Chen et al. |
| 2016/0298074 A1 | 10/2016 | Dai |
| 2016/0367991 A1 | 12/2016 | Petersen et al. |
| 2017/0029805 A1 | 2/2017 | Li et al. |
| 2017/0218355 A1 | 8/2017 | Buie et al. |
| 2017/0283761 A1 | 10/2017 | Corso |
| 2017/0307606 A1 | 10/2017 | Hallock |
| 2017/0349874 A1 | 12/2017 | Jaques et al. |
| 2018/0023045 A1 | 1/2018 | Hallock et al. |
| 2018/0028567 A1 | 2/2018 | Li et al. |
| 2018/0051327 A1 | 2/2018 | Blainey et al. |
| 2018/0112235 A1 | 4/2018 | Li et al. |
| 2018/0169148 A1 | 6/2018 | Adair et al. |
| 2018/0179485 A1 | 6/2018 | Borenstein et al. |

FOREIGN PATENT DOCUMENTS

| | | |
|---|---|---|
| EP | 2395087 | 12/2011 |
| EP | 3030652 | 6/2016 |
| EP | 1766004 | 8/2016 |
| EP | 2459696 | 11/2017 |
| WO | WO 2003/057819 | 7/2001 |
| WO | WO 2003/087341 | 10/2003 |
| WO | WO 2009/094578 | 7/2009 |
| WO | WO 2010079430 | 7/2010 |
| WO | WO 2011/072246 | 6/2011 |
| WO | WO 2013/176772 | 11/2013 |
| WO | WO 201/5021270 | 2/2015 |
| WO | WO 2016/003485 | 1/2016 |
| WO | WO 2016/054939 | 4/2016 |
| WO | WO 2016/145290 | 9/2016 |
| WO | WO 2017/078631 | 5/2017 |
| WO | WO 2018/015544 | 1/2018 |
| WO | WO 2018/191715 | 10/2018 |

OTHER PUBLICATIONS

International Search Report and Written Opinion for International Application No. PCT/US2018/053670, dated Jan. 3, 2019, p. 1-13.

International Search Report and Written Opinion for International Application No. PCT/US2018/53671, dated Sep. 26, 2018, p. 1-12.

International Search Report and Written Opinion for International Application No. PCT/US2018/040519, dated Sep. 26, 2018, p. 1-8.

First Office Action Interview Pilot Program Pre-Interview Communication for U.S. Appl. No. 16/024,831, dated Feb. 12, 2019, p. 1-37.

NonFinal Office Action for U.S. Appl. No. 16/024,816 dated Sep. 4, 2018, p. 1-10.

Final Office Action for U.S. Appl. No. 16/024,816 dated Nov. 26, 2018, p. 1-12.

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids.Research, 41(7):4336-43 (2013).

Eklund, et al., "Altered target site specificity variants of the I-Ppol His-Cys bis homing endonuclease" Nucleic Acids Research, 35(17):5839-50 (2007).

Garst, et al., "Genome-wide mapping of mutations at single-nucleotide resolution for protein, metabolic and genome engineering", Nature Biotechnology, 35(1):48-59 (2017).

Boles, et al., "Digital-to-biological converter for on-demand production of biologics", Nature Biotechnology, doi:10.1038/nbt.3859 (May 29, 2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Pines, et al., "Codon Compression Algorithms for Saturation Mutagenesis", ACS Synthetic Biology, 4:604-14 (2015).

Verwaal, et al., "CRISPR/Cpfl enables fast and simple genome editing of *Saccharamyces cerevisiae*", Yeast, 35:201-11 (2018).

(56) References Cited

OTHER PUBLICATIONS

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt. 4137, pp. 1-16 (2018).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Cramer et al., "Functional association between promoter structure and transcript alternative splicing," PNAS USA, 94(21):11456-60 (1997).
Dalphin et al., "Transterm: A Database of Translational Signals," Nucl. Acids Res., 24(1): 216-218 (1996).
Datsenko and Wanner, "One-step inactivation of chromosomal genes in *Escherichia coli* K-12 using PCR products", PNAS USA, 97(12):6640-5 (2000).
De Kok et al., "Rapid and reliable DNA assembly via ligase cycling reaction," ACS Synth Biol., 3(2):97-106 (2014).
Desmet et al., "Human Splicing Finder: an online bioinformatics tool to predict splicing signals," Nucleic Acids Res., 37(9):e67 (2009).
Divina et al., "Ab Initio prediction of mutation-induced cryptic splice-site activation and exon skipping," European Journal of Human Genetics, 17:759-765 (2009).
Dong, "Establishment of a highly efficient virus-inducible CRISPR/Cas9 system in insect cells," Antiviral Res., 130:50-7(2016).
Durai et al., "Zinc finger nucleases: custom-designed molecular scissors for genome engineering of plant and mammalian cells", Nucleic Acids Res., 33(18):5978-90 (2005).
Engler et al., "PLoS One, A One Pot, One Step, Precision Cloning Method with High Throughput Capability," 3(11):e3647 (2008).
Epinat et al., "A novel engineered meganuclease induces homologous recombination in eukaryotic cells, e.g., yeast and mammalian cells", Nucleic Acids Research, 31(11): 2952-2962.
Faber et al., "Genome-wide prediction of splice-modifying SNPs in human genes using a new analysis pipeline called AASsites," BMC Bioinformatics, 12(suppl 4):S2 (2011).
Farasat et al., "A Biophysical Model of CRISPR/Cas9 Activity for Rational Design of Genome Editing and Gene Regulation," PLoS Comput Biol., 29:12(1):e1004724 (2016).
Adamo, et al., "Flow-through comb electroporation device for delivery of macromolecules", Analytical Chemistry, 85(3):1637-41 (2015).

Greger et al., "Balancing transcriptional interference and initiation on the GAL7 promoter of *Saccharomyces cerevisiae*," PNAS, 97(15):8415-20 (2000).
Juan et al., "Histone deacetylases specifically down-regulate p53-dependent gene activation," Journal of Biological Chemistry 275.27 (2000): 20436-20443.
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1):81-9 (2009).
Lefevre et al., "Alanine-stretch scanning mutagenesis: a simple and efficient method to probe protein structure and function, " Nucleic Acids Research, vol. 25(2):447-448 (1997).
Liu et al., "A chemical-inducible CRISPR-Cas9 system for rapid control of genome editing", Nature Chemical Biology, 12:980-987(2016).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Mullick et al., "The cumate gene-switch: a system for regulated expression in mammalian cells", BMC Biotechnology, 6:43 (2006).
Nalla et al., "Automated splicing mutation analysis by information theory," Hum. Mutat., 25:334-342 (2005).
No et al., "Ecdysone-inducible gene expression in mammalian cells and transgenic mice," PNAS, 93(8):3346-3351 (1996).
Ohtsuka, "Lantibiotics: mode of action, biosynthesis and bioengineering," Curr Pharm Biotechnol, 10(2):244-51 (2009).
Patron, "DNA assembly for plant biology: techniques and tools," Curr Opinion Plant Biol., 19:14-9 (2014).
Sands et al., "Overview of Post Cohen-Boyer Methods for Single Segment Cloning and for Multisegment DNA Assembly," Curr Protoc Mol Biol., 113:3.26.1-3.26.20 (2016).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
West et al., "Molecular Dissection of Mammalian RNA Polymerase II Transcriptional Termination," Mol Cell. 29(5):600-10 (2008).
West et al., "Transcriptional Termination Enhances Protein Expression in Human Cells," Mol Cell.; 33(3-9); 354-364 (2009).
International Search Report and Written Opinion for International Application No. PCT/US2019/023342 dated Jun. 6, 2019, p. 1-12.
First Office Action Interview Pilot Program Pre-Interview Communication for U.S. Appl. No. 16/360,404 dated Jul. 1, 2019, p. 1-27.
First Office Action Interview Pilot Program Pre-Interview Communication for U.S. Appl. No. 16/360,423 dated Jul. 1, 2019, p. 1-27.

\* cited by examiner

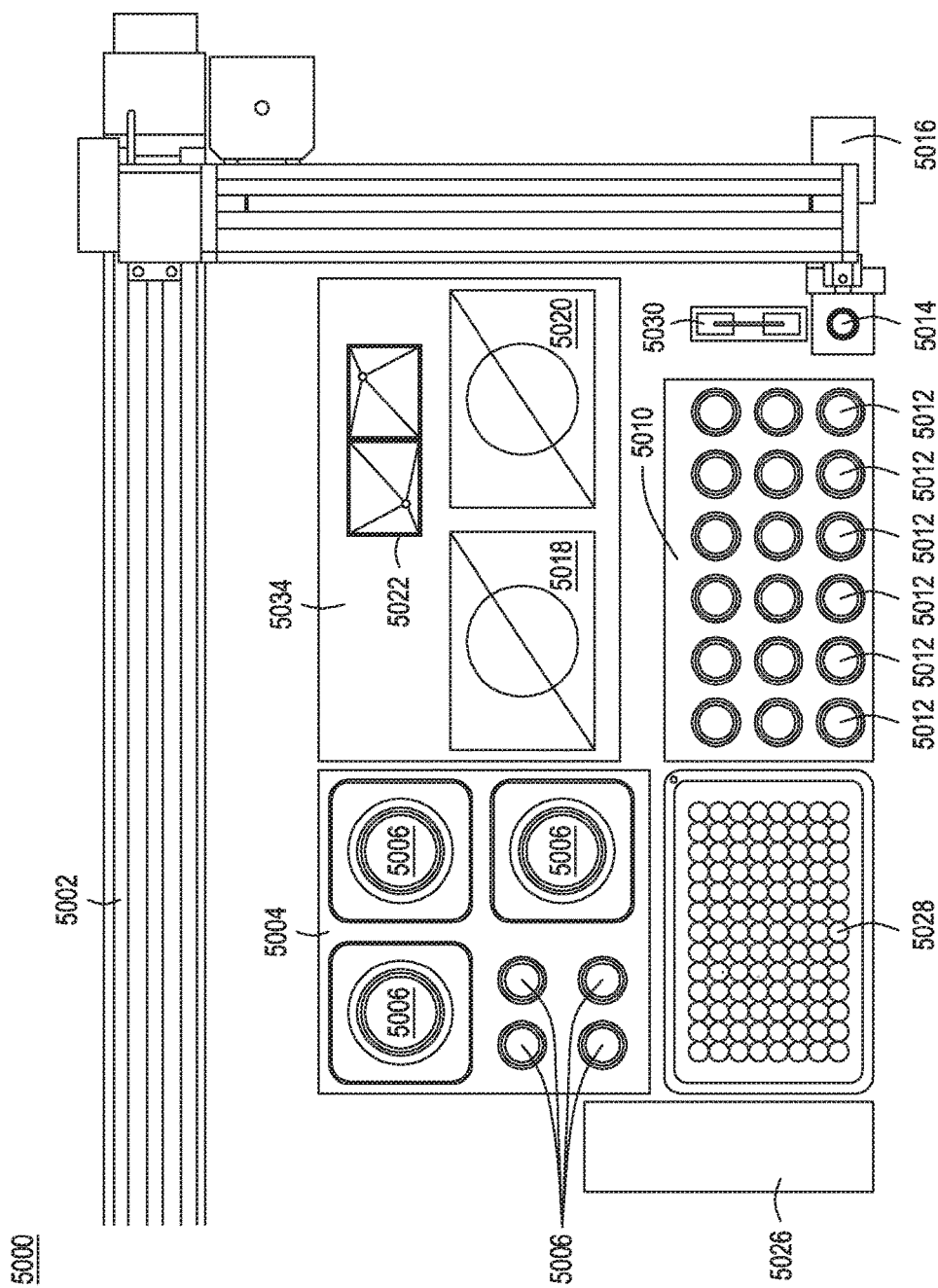

US 10,435,662 B1

AUTOMATED CONTROL OF CELL GROWTH RATES FOR INDUCTION AND TRANSFORMATION

CROSS REFERENCE TO RELATED APPLICATIONS

The present application claims priority to U.S. Provisional Patent Application No. 62/649,731, filed Mar. 29, 2018, and U.S. Provisional Patent Application No. 62/671,385, filed May 14, 2018 and are both incorporated herein by reference.

FIELD OF THE INVENTION

The present disclosure relates to methods, devices, and instruments for automated control of cell growth rates and subsequent cell processing. The devices can be used as stand-alone cell growth devices or as one module in an automated cell processing environment.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Optical density (OD), measured in a spectrophotometer, can be used as a measure of the concentration of cells in suspension. As visible light passes through a cell suspension, the light is scattered. Greater scatter indicates that more cells are present. Typically when working with a particular type of cell, one determines optical density at a particular wavelength that correlates with the growth media used. For bacteria, generally cells are grown in, e.g., LB broth, and $OD_{600}$ is measured.

To determine the OD of a cell culture, typically a quartz cuvette is used with a benchtop spectrophotometer. A wavelength is selected on the spectrophotometer, and a cuvette containing a control liquid (e.g., a blank)—almost always the growth medium in which the cells are being incubated—is inserted into the sample compartment within the spectrophotometer. A transmittance/absorbance control is then set to 100% transmittance. Once the control is adjusted for 100% transmittance, turbidity measurements can be made. The blank is removed, and then an aliquot of the sample to be measured is pipetted into another cuvette and the cuvette is inserted into the sample compartment. The spectrophotometer will then indicate the OD and percent transmittance of the sample. One drawback to using this traditional method for measuring OD is that it requires human intervention; that is, aliquots of the sample to be measured must be taken at intervals, loaded into cuvettes, and inserted into the spectrophotometer to get a reading. Not only does this procedure require time and effort, but invasively accessing the growing cell culture runs a risk that the cell culture may be contaminated. Further, the cell culture is depleted with each sample removed. An additional drawback is that once the cells are growing, it is difficult to predict when the cells will reach a target OD.

Accordingly, there is a need in the art for a cell growth device that noninvasively, rapidly, predictably and reproducibly promotes growth in a variety of cell types while automatically measuring the OD of the cells in the vessel in which they are growing. Additionally, there is a need in the art for a cell growth device that controls the growth of the cells to a target OD at a target time as requested by a user. Such a cell growth device can function either as a stand-alone device, e.g., benchtop device, or the cell growth device can be employed as one module in a multi-module automated cell processing system. The disclosed cell growth devices and methods address these needs.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

Provided herein are methods, devices, and instruments for automated control of cell growth rates where growth of the cells is measured in situ. The devices can be used as a stand-alone device or as one module in an automated environment, e.g., as one module in multi-module cell processing environment. The cell growth device includes a temperature-controlled rotating growth vial, a motor assembly to spin the vial, a spectrophotometer for measuring, e.g., OD in the vial, and a processor to accept input from a user and control the growth rate of the cells. The cell growth devices and associated methods noninvasively, rapidly, predictably and reproducibly promote growth in a variety of cell types. The methods and devices described herein automatically measure the OD of the growing cells in the rotating growth vial continuously or at set intervals and control the growth of the cells to a target OD and a target time as specified by the user. That is, the methods and devices described herein provide a feedback loop that monitors cell growth in real time and adjusts the temperature of the rotating growth vial in real time to reach the target OD at a target time specified by a user.

Thus, some embodiments provide a rotating growth vial comprising: a vial; a motor assembly configured to connect to a motor and spin the vial; an electrical connection configured to be electrically coupled to a thermal control device; a light path through the vial configured to allow light generated from a spectrophotometer to measure and deliver to a processor a value of a characteristic of cells in the vial; and a connection with the processor, wherein the processor accepts input from a user, receives from the spectrophotometer the measure of the value of the characteristic of the cells, and directs the thermal control device to adjust the temperature of the vial to grow the cells in the vial to a target value at a target time. In some aspects, the rotating growth vial has two or more "paddles" or interior features disposed within the rotating growth vial. In some aspects, the width of the paddles or interior features varies with the size or volume of the rotating growth vial, and may range from $\frac{1}{20}$ to just over $\frac{1}{3}$ the diameter of the rotating growth vial, or from $\frac{1}{15}$ to $\frac{1}{4}$ the diameter of the rotating growth vial, or from $\frac{1}{10}$ to $\frac{1}{5}$ the diameter of the rotating growth vial. In some aspects, the length of the paddles varies with the size or volume of the rotating growth vial, and may range from $\frac{4}{5}$ to $\frac{1}{4}$ the length of the main body of the rotating growth vial, or from $\frac{3}{4}$ to $\frac{1}{3}$ the length of the main body of the rotating growth vial, or from $\frac{1}{2}$ to $\frac{1}{3}$ the length of the main body of the rotating growth vial. In other aspects, there may be concentric rows of raised features disposed on the inner surface of the main body of the rotating growth vial arranged horizontally or vertically; and in other aspects, there may be a spiral configuration of raised features disposed on the inner surface of the main body of the rotating growth vial. In alternative aspects, the concentric rows of raised features or spiral configuration may be disposed upon a post or center structure of the rotating growth vial.

In some aspects of the rotating growth vial, the characteristic that is measured is optical density. In some aspects the wavelength at which the optical density is measured is selected by a user. In some aspects the characteristic is measured continuously, and in other aspects, the characteristic is measured at intervals. In some aspects the rotating growth vial comprises a second light path. In some aspects the rotating cell growth vial volume is 1-250 ml, 2-100 ml, or 12-35 ml. In some aspects the vial is fabricated from cyclic olefin copolymer (COC), polycarbonate, or polypropylene, and may be fabricated by injection molding.

Additionally, some embodiments provide a cell growth device that comprises a housing; a motor; a thermal control device; a spectrophotometer; a processor; and a rotating cell growth vial comprising a vial; a motor assembly configured to be connected to the motor to spin the vial; an electrical connection configured to be electrically coupled to the thermal control device; a first light path through the vial to measure a value of a characteristic of cells in the vial via the spectrophotometer; and a connection to the processor, wherein the processor accepts input from a user, receives from the spectrophotometer the value of the characteristic of the cells, calculates the control actions, and directs the thermal control device to adjust the temperature of the vial to grow the cells to a target value at a target time. Also in some aspects, the thermal control device may adjust the temperature of the rotating growth vial for, in addition to cell growth, heat shock of the culture, induction of temperature-sensitive inducible promoters, and for cooling and maintaining the growth culture at, e.g., 4° C.

In some aspects, the characteristic that is measured is optical density. In some aspects, the wavelength at which the optical density is measured is part of a script that is programmed into the processor, and in other aspects the wavelength at which the optical density is measured is specified by a user. In some aspects, the characteristic is measured continuously, and in other aspects, the characteristic is measured at intervals. In yet other aspects of this embodiment, the characteristic is measured at intervals until a specified value is met, then the characteristic is measured continuously. In some aspects the rotating cell growth vial component of the cell growth device comprises a second light path different from the first light path to measure the value of the characteristic of cells in the vial via the spectrophotometer.

In some aspects the motor component of the cell growth device is configured to hold a constant revolution per minute between 0 and 3000 RPM, and in some aspects, the motor comprises directional control. In some aspects the motor is configured to oscillate the rotating growth vial in opposite directions, e.g., clockwise then counter-clockwise revolutions. In some aspects the thermal control device component of the cell growth device is a Peltier device.

In some aspects of the cell growth device, the processor is configured to notify the user when the cells have reached the target value by, e.g., a text such as an SMS (Simple Message System standard) text, email or other messages delivered to a tablet, smart phone, or other PDA.

In some aspects the processor component is programmed with information to be used as a blank or control to which the value of the characteristic of the cells is compared.

Additionally, a multi-module cell processing system comprising the cell growth device is provided. In some aspects, the multi-module cell processing system further comprises a cell concentration module, a protein induction module, a transformation module, an editing module, a recovery module, and/or a storage module.

In some aspects the cell growth device is a first module in a cell growth, cell concentration, and cell transformation multi-module instrument.

Also presented herein is a method for using the cell growth device comprising: transferring an aliquot of cells into a hermetically-sealed, media-filled cell growth vial; entering a user-preferred target characteristic value and user-preferred time to reach the user-preferred target characteristic value into the processor; spinning the vial; measuring the characteristic value of the cells; adjusting the temperature according to the user-preferred time; determining when the cells reach the user-preferred characteristic value of the cells; cooling the cell growth vial or advancing cells to a next module in an automated multi-module cell processing system; and notifying a user that the cells have reached the characteristic value.

In some aspects, the method further comprises performing the measuring, adjusting, and determining steps until the cells reach the user-preferred value of the cells. In some aspects, the characteristic measured is optical density (where the range measured can be OD 0.1 to OD 10), and in some aspects the user-preferred target characteristic value is 2.7 and the target characteristic value is read at OD600.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 5 depicts an exemplary automated multi-module cell processing instrument comprising the growth module.

It should be understood that the drawings are not necessarily to scale, and that like reference numbers refer to like features.

DETAILED DESCRIPTION

Figure 1A:
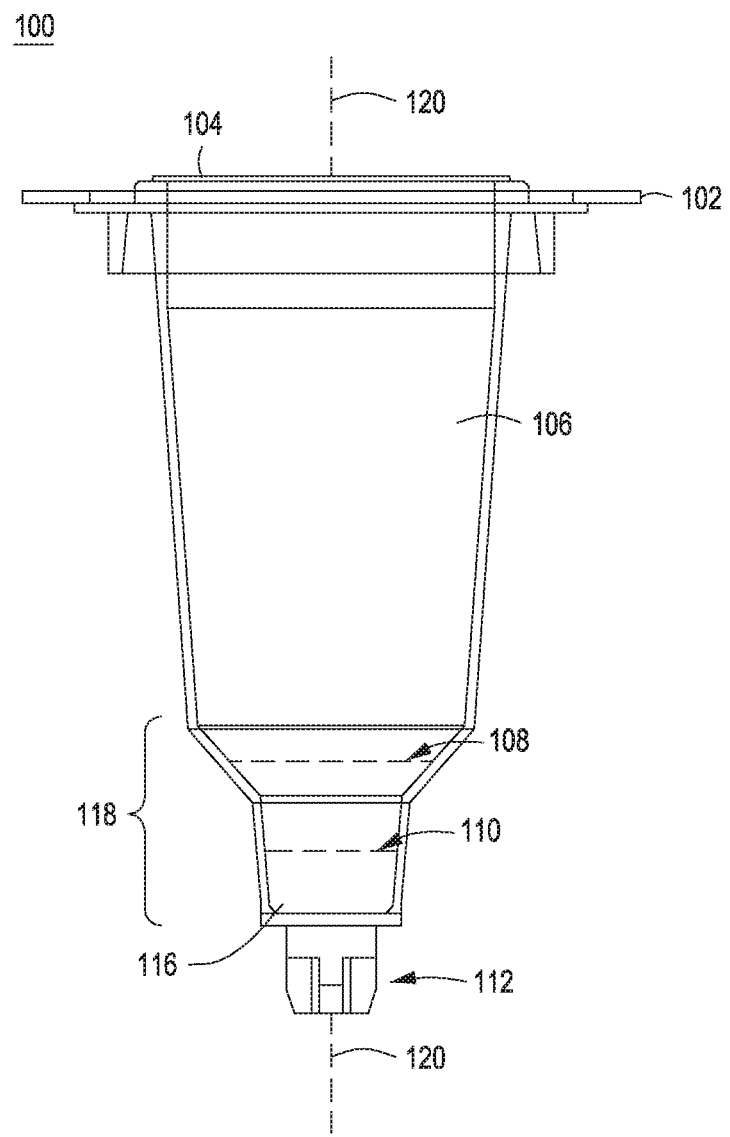
FIG. 1A depicts one embodiment of a rotating growth vial for use with the cell growth device described herein.

All of the functionalities described in connection with one embodiment of the methods, devices and instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual.* 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes. Nucleic acid-guided nuclease techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The Invention in General

For culture of adherent cells, cells may be disposed on beads, microcarriers, or other type of scaffold suspended in medium. Most normal mammalian tissue-derived cells—except those derived from the hematopoietic system—are anchorage dependent and need a surface or cell culture support for normal proliferation. In the rotating growth vial described herein, microcarrier technology is leveraged. Microcarriers of particular use typically have a diameter of 100-300 µm and have a density slightly greater than that of the culture medium (thus facilitating an easy separation of cells and medium for, e.g., medium exchange) yet the density must also be sufficiently low to allow complete suspension of the carriers at a minimum stirring rate in order to avoid hydrodynamic damage to the cells. Many different types of microcarriers are available, and different microcarriers are optimized for different types of cells. There are positively charged carriers, such as Cytodex 1 (dextran-based, GE Healthcare), DE-52 (cellulose-based, Sigma-Aldrich Labware), DE-53 (cellulose-based, Sigma-Aldrich Labware), and HLX 11-170 (polystyrene-based); collagen- or ECM- (extracellular matrix) coated carriers, such as Cytodex 3 (dextran-based, GE Healthcare) or HyQ-sphere Pro-F 102-4 (polystyrene-based, Thermo Scientific); non-charged carriers, like HyQ-sphere P 102-4 (Thermo Scientific); or macroporous carriers based on gelatin (Cultisphere, Percell Biolytica) or cellulose (Cytopore, GE Healthcare).

For culture of adherent cells, cells may be disposed on beads or another type of scaffold suspended in medium. Most normal mammalian tissue-derived cells—except those derived from the hematopoietic system—are anchorage dependent and need a surface or cell culture support for normal proliferation. In the rotating growth vial described herein, microcarrier technology is leveraged. Microcarriers of particular use typically have a diameter of 100-300 µm and have a density slightly greater than that of the culture medium (thus facilitating an easy separation of cells and medium for, e.g., medium exchange) yet the density must also be sufficiently low to allow complete suspension of the carriers at a minimum stirring rate in order to avoid hydrodynamic damage to the cells. Many different types of microcarriers are available, and different microcarriers are optimized for different types of cells. There are positively charged carriers, such as Cytodex 1 (dextran-based, GE Healthcare), DE-52 (cellulose-based, Sigma-Aldrich Labware), DE-53 (cellulose-based, Sigma-Aldrich Labware), HLX 11-170 (polystyrene-based); collagen or ECM (extracellular matrix) -coated carriers, such as Cytodex 3 (dextran-based, GE Healthcare) or HyQ-sphere Pro-F 102-4 (polystyrene-based, Thermo Scientific); non-charged carriers, like HyQspheres P 102-4 (Thermo Scientific); or macroporous carriers based on gelatin (Cultisphere, Percell Biolytica) or cellulose (Cytopore, GE Healthcare).

Measuring the OD of a cell culture is important for vital procedures such as transformation and transfection of cells (collectively referred to generally as "transformation" herein), induction of protein production in cells, and conducting minimal inhibitory concentration experiments. Optical density may be determined as the absolute value of the logarithm with base 10 of the power transmission factor of an optical attenuator: OD=−log 10 (power out/power in). OD is optical attenuation; that is, the sum of absorption, scattering and reflection, thus OD specifies the overall power transmission. As cells grow and become denser, the OD of the cell culture increases.

In the cell growth devices described herein, in one embodiment cells are inoculated (pipetted) into a rotating growth vial pre-filled with growth media. The rotating growth vial is hermetically sealed with a foil top, and the pipette is used to punch through the foil top. An incubation (e.g., growth) temperature is set by the user or via a pre-programmed protocol by the processor, typically 30° C., and the processor initiates rotation of the rotating growth vial by the motor. The cell culture (cells+growth medium) slowly moves vertically up the wall of the rotating growth vial due to centrifugal force. The movement of the cell culture up the wall of the vial exposes a large surface area of the cell culture to oxygen in the environment (aeration) to optimize uniform cellular respiration. The cell growth device takes either continuous OD readings, OD readings at set intervals, or, e.g., takes OD readings at set intervals followed by continuous OD monitoring as the OD gets closer to the target OD. The cell growth device provides a feedback loop that monitors cell growth in real time and adjusts the temperature of the rotating growth vial in real time to reach the OD at a time specified by a user, as well as terminates the growth of the cell culture at a pre-determined OD and cools the cell culture to inhibit further growth. Optionally, the processor of the cell growth device will notify one or more users when the cells reach the target OD, e.g., via a smart phone, tablet or other device.

Thus, the cell growth device described herein enhances the growth of cells by providing rotation and aeration of the growing cells and provides in situ continuous growth rate monitoring within the temperature-controlled vial. Additionally, the processor may control a thermal control device to adjust the temperature of the rotating growth vial for, in addition to cell growth, heat shock of the culture, induction of temperature-sensitive inducible promoters, and for cooling and maintaining the cell culture at, e.g., 4° C.

The Rotating Growth Vial

FIG. 1A shows one embodiment of a rotating growth vial 100 for use with the cell growth device described herein. The rotating growth vial is an optically-transparent container having an open end 104 for receiving liquid media and cells, a central vial region 106 that defines the primary container for growing cells, a tapered-to-constricted region 118 defining at least one light path 110, a closed end 116, and a drive engagement mechanism 112. The rotating growth vial has a central longitudinal axis 120 around which the vial rotates, and the light path 110 is generally perpendicular to the longitudinal axis of the vial. The first light path 110 is positioned in the lower constricted portion of the tapered-to-constricted region 118. Optionally, some embodiments of the rotating growth vial 100 have a second light path 108 in the tapered region of the tapered-to-constricted region 118. Both light paths in this embodiment are positioned in a region of the rotating growth vial that is constantly filled with the cell culture (cells+growth media) and is not affected by the rotational speed of the growth vial. The first light path 110 is shorter than the second light path 108 allowing for sensitive measurement of OD values when the OD values of the cell culture in the vial are at a high level (e.g., later in the cell growth process), whereas the second light path 108 allows for sensitive measurement of OD values when the OD values of the cell culture in the vial are at a lower level (e.g., earlier in the cell growth process).

The drive engagement mechanism 112 engages with a motor (not shown) to rotate the vial. In some embodiments, the motor drives the drive engagement mechanism 112 such that the rotating growth vial is rotated in one direction only, and in other embodiments, the rotating growth vial is rotated in a first direction for a first amount of time or periodicity, rotated in a second direction (i.e., the opposite direction) for a second amount of time or periodicity, and this process may be repeated so that the rotating growth vial (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial may be oscillated at a first periodicity (e.g., every 60 seconds), and then a later stage of cell growth the rotating growth vial may be oscillated at a second periodicity (e.g., every one second) different from the first periodicity.

The rotating growth vial 100 may be reusable or, preferably, the rotating growth vial is consumable. In some embodiments, the rotating growth vial is consumable and is presented to the user pre-filled with growth medium, where the vial is hermetically sealed at the open end 104 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 104 may optionally include an extended lip 102 to overlap and engage with the cell growth device (not shown). In automated systems, the rotating growth vial 100 may be tagged with a barcode or other identifying means that can be read by a scanner or camera that is part of the automated system (not shown).

The volume of the rotating growth vial 100 and the volume of the cell culture (including growth medium) may vary greatly, but the volume of the rotating growth vial 100 must be large enough to generate a specified total number of cells. In practice, the volume of the rotating growth vial 100 may range from 1-250 ml, 2-100 ml, from 5-80 ml, 10-50 ml, or from 12-35 ml. Likewise, the volume of the cell culture (cells+growth media) should be appropriate to allow proper aeration and mixing in the rotating growth vial. Proper aeration promotes uniform cellular respiration within the growth media. Thus, the volume of the cell culture should be approximately 5-85% of the volume of the growth vial or from 20-60% of the volume of the growth vial. For example, for a 30 ml growth vial, the volume of the cell culture would be from about 1.5 ml to about 26 ml, or from 6 ml to about 18 ml.

The rotating growth vial 100 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyamide, polyethylene, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 1B:
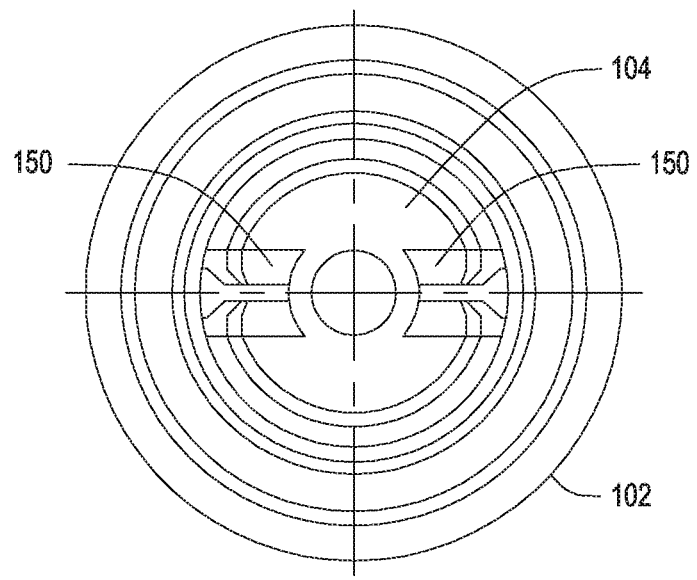
FIG. 1B is a top view of a second embodiment of a rotating growth vial for use with the cell growth device described herein.
Figure 1C:
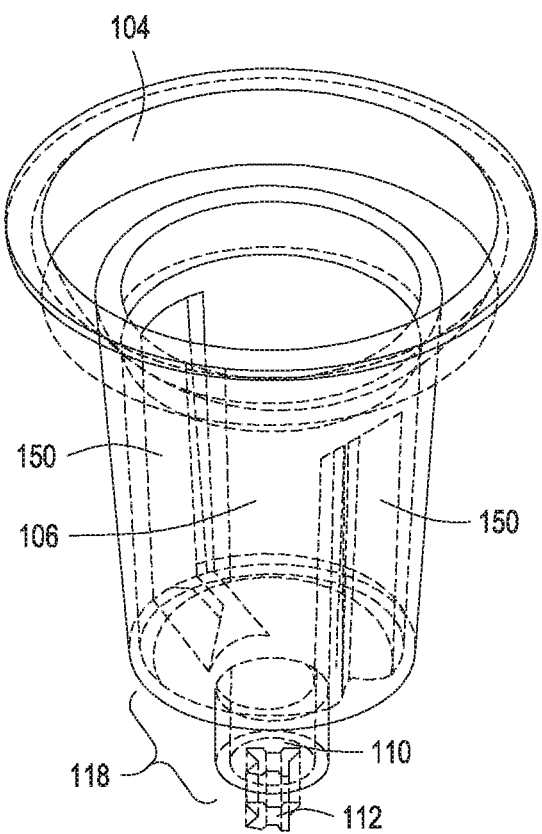
FIG. 1C is a side perspective view of the rotating growth vial of FIG. 1B.
Figure 1D:
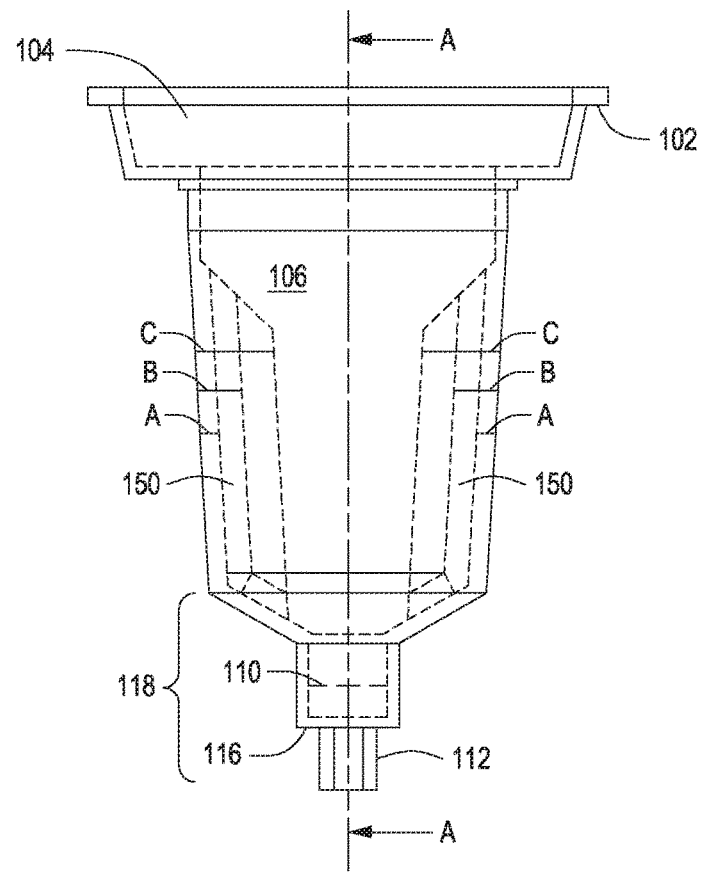
FIG. 1D is a side view of the rotating growth vial depicted in FIGS. 1B and 1C.

FIGS. 1B-1D show a second embodiment of a rotating growth vial for use with the cell growth device. FIG. 1B is a top view of the second embodiment of a rotating growth vial 100. As in FIG. 1A, the rotating growth vial is an optically transparent container having an open end 104 for receiving liquid media and cells. Also shown is extended lip 102 configured to overlap and engage with the cell growth device (not shown) and to allow a grip for a user to insert and remove the rotating growth vial from the cell growth device. In this second embodiment of the rotating growth vial, two inner "paddles" 150 can be seen extending from the inner wall of the rotating growth vial toward the center of the central vial region 106.

FIG. 1C is a side perspective view of the second embodiment of a rotating growth vial shown in FIG. 1B. As in FIG. 1A, the rotating growth vial is a transparent container having an open end 104 for receiving liquid media and cells, a central vial region 106 that defines the primary container for growing cells, a tapered-to-constricted region 118 defining at least one light path 110, and a drive engagement mechanism 112. The light path 110 is positioned in the lower constricted portion of the tapered-to-constricted region 118 and is positioned in a region of the rotating growth vial that is constantly filled with the cell culture (cells+growth media) and is not affected by the rotational speed of the growth vial. The drive engagement mechanism 112 engages with a motor (not shown) to rotate the vial. Also shown in FIG. 1C are paddles 150 extending from the inner wall of the rotating growth vial toward the center of the central vial region 106.

FIG. 1D is a side view of the rotating growth vial of FIGS. 1B and 1C which more clearly show the paddles or interior features of the rotating growth vial. FIG. 1D shows a rotating growth vial with a central vial region 106 that defines the primary container for growing cells, a tapered-to-constricted region 118 defining at least one light path 110, a closed end 116, and a drive engagement mechanism 112. The rotating growth vial has a central longitudinal axis A-A around which the vial rotates. The light path 110 is generally perpendicular to the longitudinal axis of the vial and is positioned in the lower constricted portion of the tapered-to-constricted region 118. The drive engagement mechanism 112 engages with a motor (not shown) to rotate the vial. Also shown in FIG. 1D are two paddles 150 extending from the inner wall of the rotating growth vial 100 toward the center of the central vial region 106. FIG. 1D shows that the widths and lengths of paddles 150 can vary; for example, the width may be short as in A, longer as in B, and even longer as in C. Preferably, the width of both paddles 150 is the same.

Figure 1E:
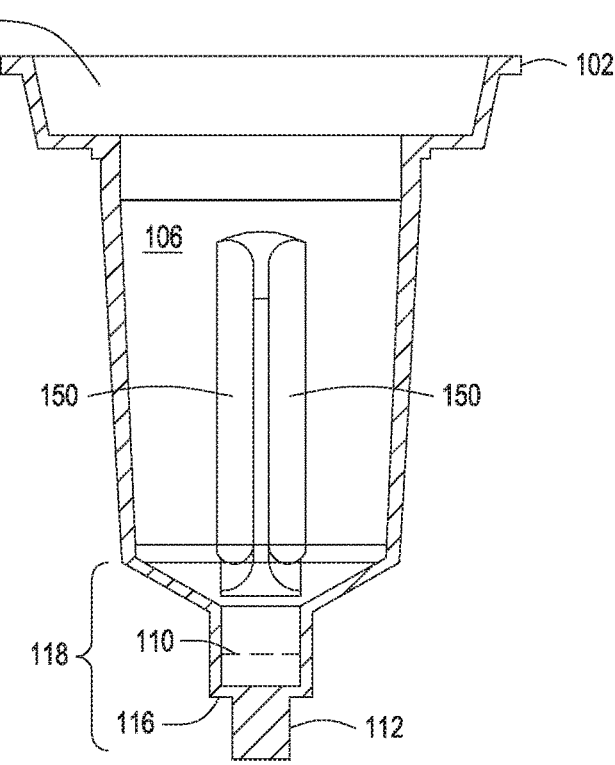
FIG. 1E is a side view of the second embodiment of the rotating growth vial shown in FIG. 1D and taken along line A-A of FIG. 1D.

FIG. 1E is a side view of the second embodiment of the rotating growth vial 100 shown in FIG. 1D and taken along line A-A of FIG. 1D and looking perpendicularly at paddle 150 the side of which is shown in FIG. 1D. Shown is central vial region 106 that defines the primary container for growing cells, a tapered-to-constricted region 118 defining at least one light path 110, a closed end 116, and a drive engagement mechanism 112. Also shown is extended lip 102 configured to overlap and engage with the cell growth device (not shown) and to allow a grip for a user to insert and remove the rotating growth vial from the cell growth device.

Like the rotating growth vial depicted in FIG. 1A, the paddle embodiment of the rotating growth vial 100 may be reusable, or preferably, the rotating growth vial is consumable. In some embodiments, the rotating growth vial 100 is consumable and is presented to the user pre-filled with growth medium, where the vial is hermetically sealed at the open end 104 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip (or needle) to punch through the foil seal of the vial. Open end 104 may optionally include an extended lip 102 to overlap and engage with the cell growth device (not shown). In automated systems, the rotating growth vial 100 may be tagged with a barcode or other identifying means that can be read by a scanner or camera that is part of the automated system (not shown).

The volume of the paddle embodiment of the rotating growth vial 100 and the volume of the cell culture (including growth medium) may vary greatly, but the volume of the paddle embodiment of the rotating growth vial 100, like a growth vial without interior features, must be large enough for the cell culture in the growth vial to get proper aeration while the vial is rotating as described above.

Although the paddle embodiment of the rotating growth vial 100 depicted in FIGS. 1B-1D shows two paddles, the rotating growth vial may comprise 2, 3, 4, 5, 6 or more paddles, and up to 20 paddles. The number of paddles will depend upon, e.g., the size or volume of the rotating growth vial 100. The paddles may be arranged symmetrically as single paddles extending from the inner wall of the vial into the interior of the vial, or the paddles may be symmetrically arranged in groups of 2, 3, 4 or more paddles in a group (for example, a pair of paddles opposite another pair of paddles) extending from the inner wall of the vial into the interior of the vial. In another embodiment, the paddles may extend from the middle of the rotating growth vial out toward the inner wall of the rotating growth vial, from, e.g., a post or other support structure in the interior of the rotating growth vial.

Similarly, the size and configuration of the paddles may vary greatly depending on the size or volume of the rotating growth vial 100. For example, FIG. 1D depicts paddles 150 of varying width A, B and C. However, these widths are exemplary only. Because the actual measurement of the paddles varies with the size or volume of the rotating growth vial 100, it is perhaps more instructive to describe the dimensions of the paddles with respect to the rotating growth vial 100. For example, in FIG. 1D, width A is approximately 1/12 the diameter of the vial, width B is approximately 1/7 the diameter of the vial, and width C is approximately 1/4 the diameter of the vial. Thus, the width of the paddles may range from 1/20 to just under 1/2 the diameter of the rotating growth vial, or from 1/15 to 1/3 the diameter of the rotating growth vial, or from 1/10 to 1/4 the diameter of the rotating growth vial. The actual measurement of the length of the paddles also will vary with the size or volume of the rotating growth vial 100, and may extend only through the central vial region 106 of the rotating growth vial 100, or may also extend into the tapered portion of the tapered-to-constricted region 118. The length of the paddles may range from 4/5 to 1/4 the length of the central vial region 106 of the rotating growth vial 100, or from 3/4 to 1/3 the length of the central vial region 106 of the rotating growth vial 100, or from 1/2 to 1/3 the length of the central vial region of the rotating growth vial 100.

The configuration or shape of the paddles or interior features may vary as well and may essentially embody any shape that may be configured into a paddle or other feature. For example, the paddles may extend perpendicularly from, e.g., the inner wall of the rotating growth vial 100, or the paddles may be curved, e.g., to the left or right of perpendicular. As shown in FIG. 1D, the end of the paddles proximal to the open end 104 of the rotating growth vial 100 may be tapered. In FIG. 1D, the end of the paddles are tapered from high to low as the paddle extends from the inner wall toward the center of the rotating growth vial 100; however, embodiments where the paddles are tapered from low to high as the paddle extends from the inner wall to the center of the rotating growth vial 100 are also contemplated, as are untampered paddles. Also shown in FIG. 1D, the paddles extend from the central vial region 106 into tapered-to-constricted region 118, although this is only one option for configuring the paddles.

In another embodiment, there may be concentric rows of raised regions disposed on the inner surface of the central vial region 106 of the rotating growth vial 100 arranged horizontally or vertically (embodiment not shown); and in another embodiment, there may be a spiral configuration of raised regions disposed on the inner surface of the central vial region 106 of the rotating growth vial 100. In alternative aspects, the concentric rows of raised regions or spiral configuration may be disposed upon a post or center structure of the rotating growth vial 100.

The paddles 150 of the rotating growth vial 100—like the rotating growth vial itself—are preferably fabricated from a bio-compatible transparent material, and the material from which the paddles are fabricated should be able to be cooled to about 4° C. or lower and heated to about 55° C. or higher to accommodate both temperature-based cell assays and long-term storage at low temperatures. Exemplary materials from which to fabricate the paddles—like the rotating growth vial 100—are listed above. Preferably, the rotating growth vial and paddles are fabricated in one piece by, e.g., injection molding or extrusion.

The Cell Growth Device

Figure 2A:
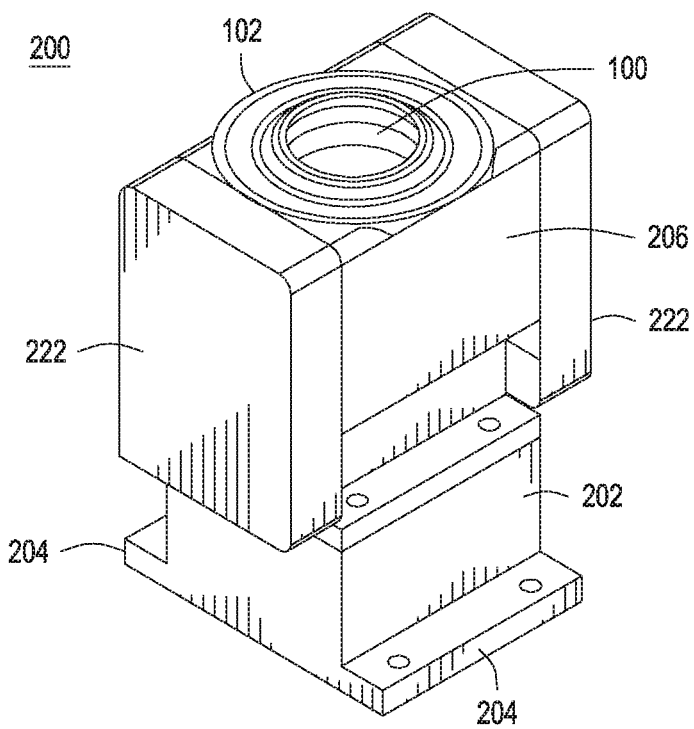
FIG. 2A illustrates a perspective view of one embodiment of a cell growth vial and housing.
Figure 2B:
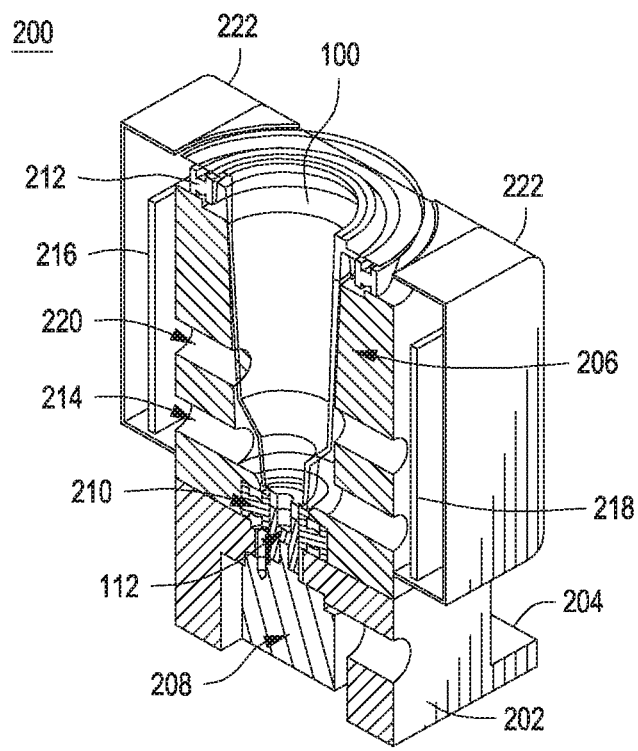
FIG. 2B depicts a cut-away view of the cell growth device from FIG. 2A.

FIG. 2A is a perspective view of one embodiment of a cell growth device 200. FIG. 2B depicts a cut-away view of the cell growth device 200 from FIG. 2A. In both figures, the rotating growth vial 100 is seen positioned inside a main housing 206 with the extended lip 102 of the rotating growth vial 100 extending above the main housing 206. Additionally, end housings 222, a lower housing 202 and flanges 204 are indicated in both figures. Flanges 204 are used to attach the cell growth device 200 to heating/cooling means or other structure (not shown). FIG. 2B depicts additional detail. In FIG. 2B, upper bearing 212 and lower bearing 210 are shown positioned in main housing 206. Upper bearing 212 and lower bearing 210 support the vertical load of rotating growth vial 100. Lower housing 202 contains the drive motor 208. The cell growth device 200 of FIG. 2B comprises two light paths: a primary light path 214, and a secondary light path 220. Light path 214 corresponds to light path 110 positioned in the constricted portion of the tapered-to-constricted portion of the rotating growth vial 100, and light path 220 corresponds to light path 108 in the tapered portion of the tapered-to-constricted portion of the rotating growth vial. Light paths 110 and 108 are not shown in FIG. 2B but may be seen in, e.g., FIG. 1A. In addition to light paths 214 and 220, there is an emission board 218 to illuminate the light path(s), and detector board 216 to detect the light after the light travels through the cell culture liquid in the rotating growth vial 100.

The motor 208 used to rotate the rotating growth vial 200 in some embodiments is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 208 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 206, end housings 222 and lower housing 202 of the cell growth device 200 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 100 is envisioned in some embodiments to be reusable, but preferably is consumable, the other components of the cell growth device 200 are preferably reusable and function as a stand-alone benchtop device or as a module in a multi-module cell processing system.

The processor (not shown) of the cell growth device 200 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor of the cell growth device 200—may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 200, where the second spectrophotometer is used to read a blank at designated intervals.

Figure 2C:
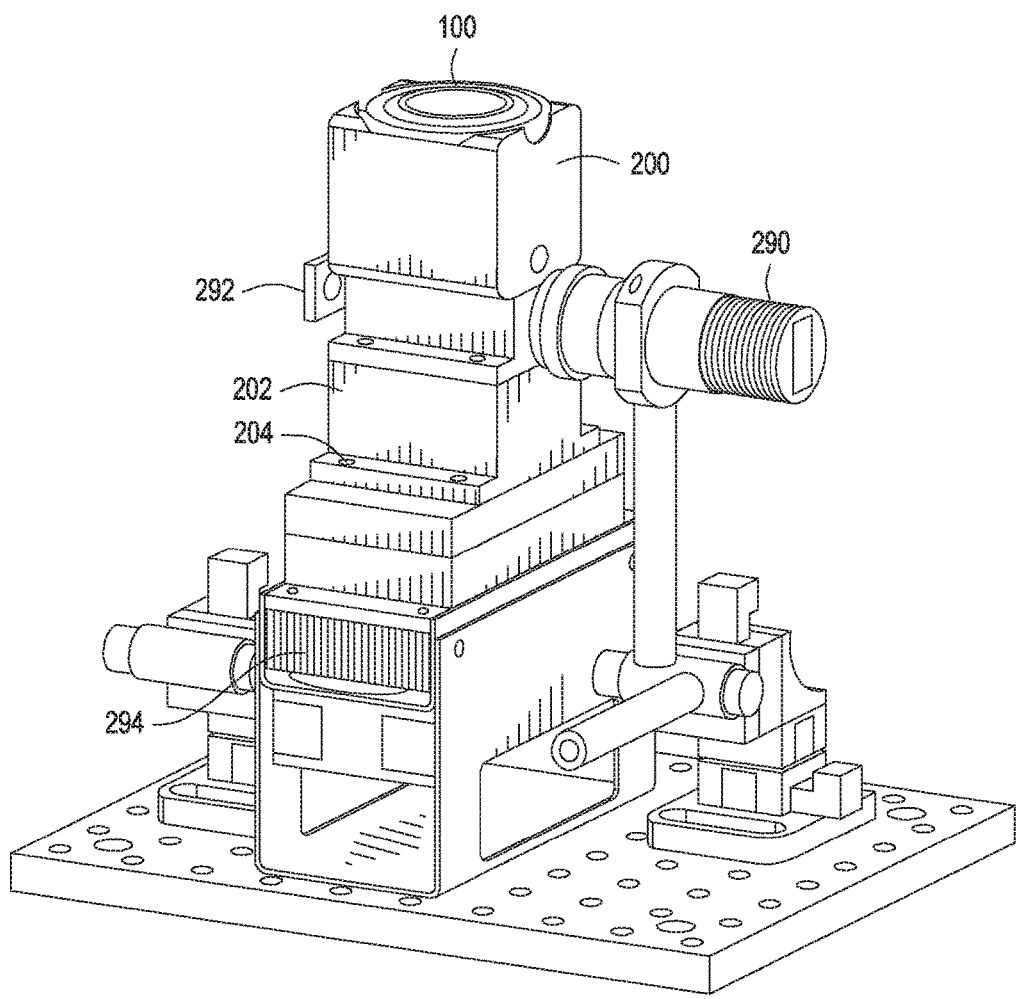
FIG. 2C illustrates the cell growth device of FIG. 2A coupled to LED, detector, and temperature regulating components.

FIG. 2C illustrates a cell growth device 200 as part of an assembly comprising the cell growth device 200 of FIG. 2A coupled to light source 290, detector 292, and thermal components 294. The rotating growth vial 100 is inserted into the cell growth device. Components of the light source 290 and detector 292 (e.g., such as a photodiode with gain control to cover 5-log) are coupled to the main housing of the cell growth device. The lower housing 202 that houses the motor that rotates the rotating growth vial 100 is illustrated, as is one of the flanges 204 that secures the cell growth device 200 to the assembly. Also, the thermal components 294 illustrated are a Peltier device or thermoelectric cooler. In this embodiment, thermal control is accomplished by attachment and electrical integration of the cell growth device 200 to the thermal component 294 via the flange 204 on the base of the lower housing 202. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 200 is controlled to approximately +/−0.5° C.

Figure 2D:
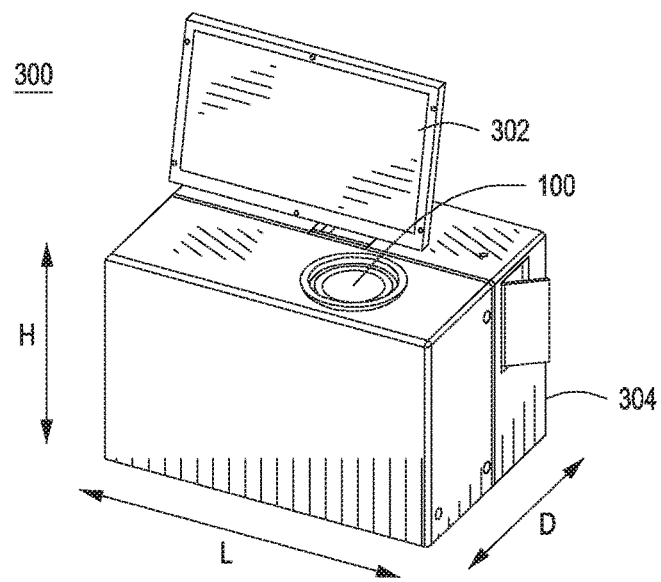
FIG. 2D illustrates a perspective view of a stand-alone cell growth device.
Figure 2E:
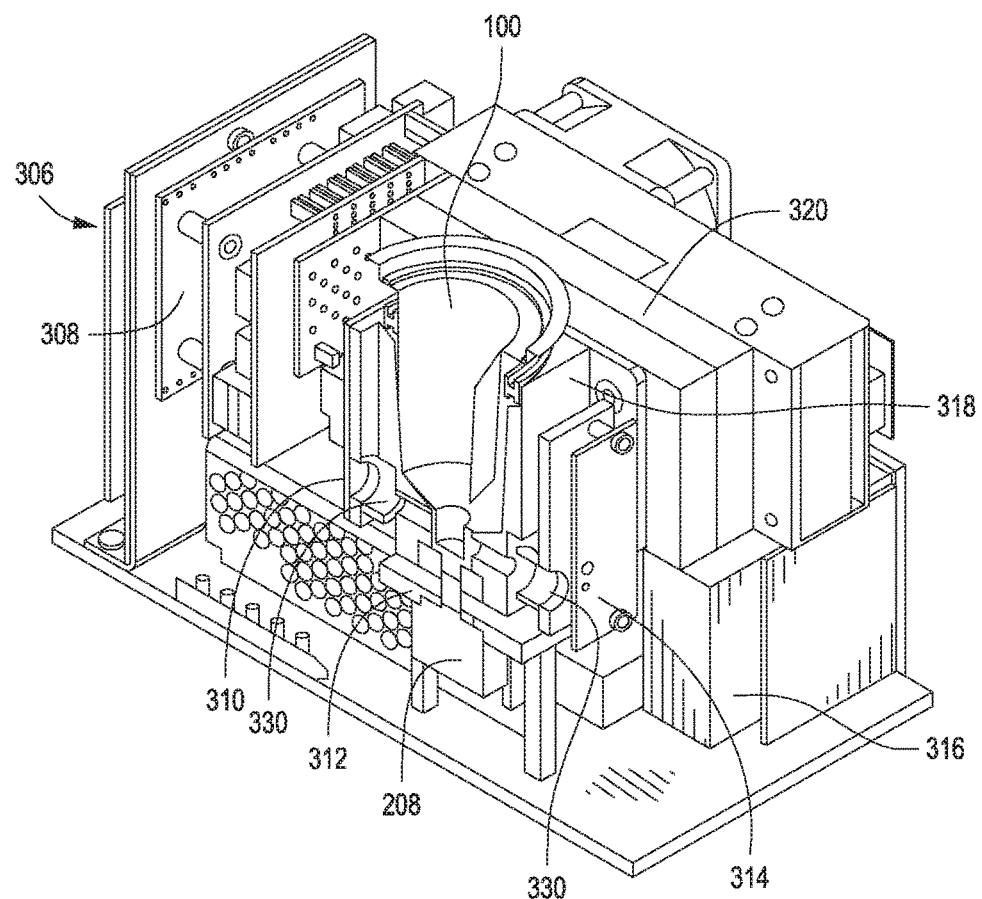
FIG. 2E illustrates a cross-section of the stand-alone cell growth device shown in FIG. 2D.

FIG. 2D is a perspective view and FIG. 2E is a cross-section of a stand-alone cell growth device 300 that has been built and tested. FIG. 2D shows the rotating growth vial 100 inserted into a housing 304 along with an LCD touch screen 302. The cell growth device 300 shown in FIG. 2D has the following dimensions: H=146 mm, L=225 mm, and D=153 mm; although these dimensions are, of course, exemplary. This embodiment of the device weighed approximately 4.05 kg, required 40 watts of power for the heating, cooling, and fan; 5 watts of power for the rotational motor; 5 watts of power for the light emitting diode and photodetector; and 5 watts of power for the single board computer and digital-analog-input-output boards (all described below). The exterior of the cell growth device 300 consists in this embodiment of a set of sheet metal case halves on a base that holds all the components necessary to run the module. A 120 VAC International Electrotechnical Commission (IEC) standard power cord (not shown) plugged into a wall outlet is all that is needed to power the unit.

In this embodiment, a rear-mounted power entry module 316 contains the safety fuses and the on-off switch, which when switched on powers the internal AC and DC power supplies (not shown) activating a built-in single board computer which runs, e.g., a Windows 10 operating system. The cell growth module in this embodiment has no wired physical external communications connections, but optional communications can be accessed via the built-in Wi-Fi interface. The cell growth module can be configured to operate remotely or by the user using the attached 7" LCD touch screen 302. Security and access controls optionally may be enabled that, e.g., require logons to activate the programs and to run the growth functions. Likewise, access via remote laptops or desktops is configurable—and if allowed on the network—parameters such as growth data, graphs, and sequence progress can be sent out at intervals via email or text messages. Any updates to programs or operating systems can be "pushed" out remotely as well, again depending on network security settings.

FIG. 2E is a cross-section of the stand-alone cell growth device shown in FIG. 2D, illustrating internal components. The major components are a thermoelectric cooler control 306 and a thermoelectric cooler 320, also known as a Peltier device, capable of heating or cooling at a 40-watt capacity. Also seen are the control electronics 308, which includes a single board computer as well as analog and digital boards attached to the main housing that contain the optical systems for making the OD measurements. A rotating growth vial housing 318 contains bearings (not shown), a drive motor 208 (e.g., a brushless DC type motor), and a drive coupling 312 which manages the thermal environment and mechanical rotation of the rotating growth vial 100. Bearings (not shown) at the top and bottom of the rotating growth vial 100 support the vertical axis of the rotating growth vial and the motor drive coupling 312 engages the rotating growth vial to allow the drive motor 208 to spin the rotating growth vial 100. A through-hole 330 is seen that allows the, e.g., 600 nm LED 310 located on the digital board control electronics 308 to illuminate through-hole 330 in the rotating growth vial housing 318, through the lower constricted section of the rotating growth vial 100, continuing through the through-hole opening 330 on the other side of the housing, and ending at analog photodiode detection board 314. The lowest section of the main housing contains the drive motor 208, in this case a brushless DC type that has built in drive controls that set and hold a constant rate of speed measured in revolutions per minute (RPM) between 0 and 3000 RPM. There is also direction control to allow programmed reversing of the rotational direction, and a tachometer output to sense actual RPM.

Thermal control is accomplished by, e.g., attachment of the housing to a Peltier device, commonly known as a thermoelectric cooler 320. Peltier devices are capable of 'pumping' heat to either side of their junctions, either cooling a surface or heating a surface depending on the direction of current flow. A thermistor is used to measure the temperature of the main housing and then through a standard electronic Proportional-Integral-Derivative (PID) controller (e.g., the temperature control board is mounted in the control electronics 308) the programmed set temperature is controlled to an accuracy of approximately +/−0.5° C. Any difference from the housing temperature (at the thermistor) and the liquid media temperature, measured inside the rotating growth vial, is pre-calibrated as an offset temperature and stored in the settings of the software control program.

Measurements of optical densities (OD) at programmed time intervals are accomplished using a 600 nm Light Emitting Diode (LED) 310 that has been columnated through an optic into the lower constricted portion of the rotating growth vial which contains the cells of interest. The light continues through a collection optic to the detection system which consists of a (digital) gain-controlled silicone photodiode 314. Generally, optical density is normally shown as the absolute value of the logarithm with base 10 of the power transmission factors of an optical attenuator: OD=−log 10 (Power out/Power in). Since OD is the measure of optical attenuation—that is, the sum of absorption, scattering, and reflection—the cell growth device OD measurement records the overall power transmission, so as the cells grow and become denser in population, the OD (the loss of signal) increases. The OD system is pre-calibrated against OD standards with these values stored in an on-board memory accessible by the measurement program.

In use, cells are inoculated (cells can be pipetted, e.g., from an automated liquid handling system or by a user) into pre-filled growth media of a rotating growth vial by piercing though the foil seal. The programmed software of the cell growth device sets the control temperature for growth, typically 30° C., then slowly starts the rotation of the rotating growth vial. The cell/growth media mixture slowly moves vertically up the wall due to centrifugal force allowing the rotating growth vial to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 200 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device has been described in the context of measuring the optical density (OD) of a growing cell culture, it should, however, be understood by a skilled artisan given the teachings of the present specification that other cell growth parameters can be measured in addition to or instead of cell culture OD. For example, spectroscopy using visible, UV, or near infrared (NIR) light allows monitoring the concentration of nutrients and/or wastes in the cell culture. Additionally, spectroscopic measurements may be used to quantify multiple chemical species simultaneously. Nonsymmetric chemical species may be quantified by identification of characteristic absorbance features in the NIR. Conversely, symmetric chemical species can be readily quantified using Raman spectroscopy. Many critical metabolites, such as glucose, glutamine, ammonia, and lactate have distinct spectral features in the IR, such that they may be easily quantified. The amount and frequencies of light absorbed by the sample can be correlated to the type and concentration of chemical species present in the sample. Each of these measurement types provides specific advantages. FT-NIR provides the greatest light penetration depth and can be used for thicker samples. FT-mid-IR (MIR) provides information that is more easily discernible as being specific for certain analytes as these wavelengths are closer to the fundamental IR absorptions. FT-Raman is advantageous when interference due to water is to be minimized. Other spectral properties can be measured via, e.g., dielectric impedance spectroscopy, visible fluorescence, fluorescence polarization, or luminescence. Additionally, the cell growth device may include additional sensors for measuring, e.g., dissolved oxygen, carbon dioxide, pH, conductivity, and the like.

Figure 2F:
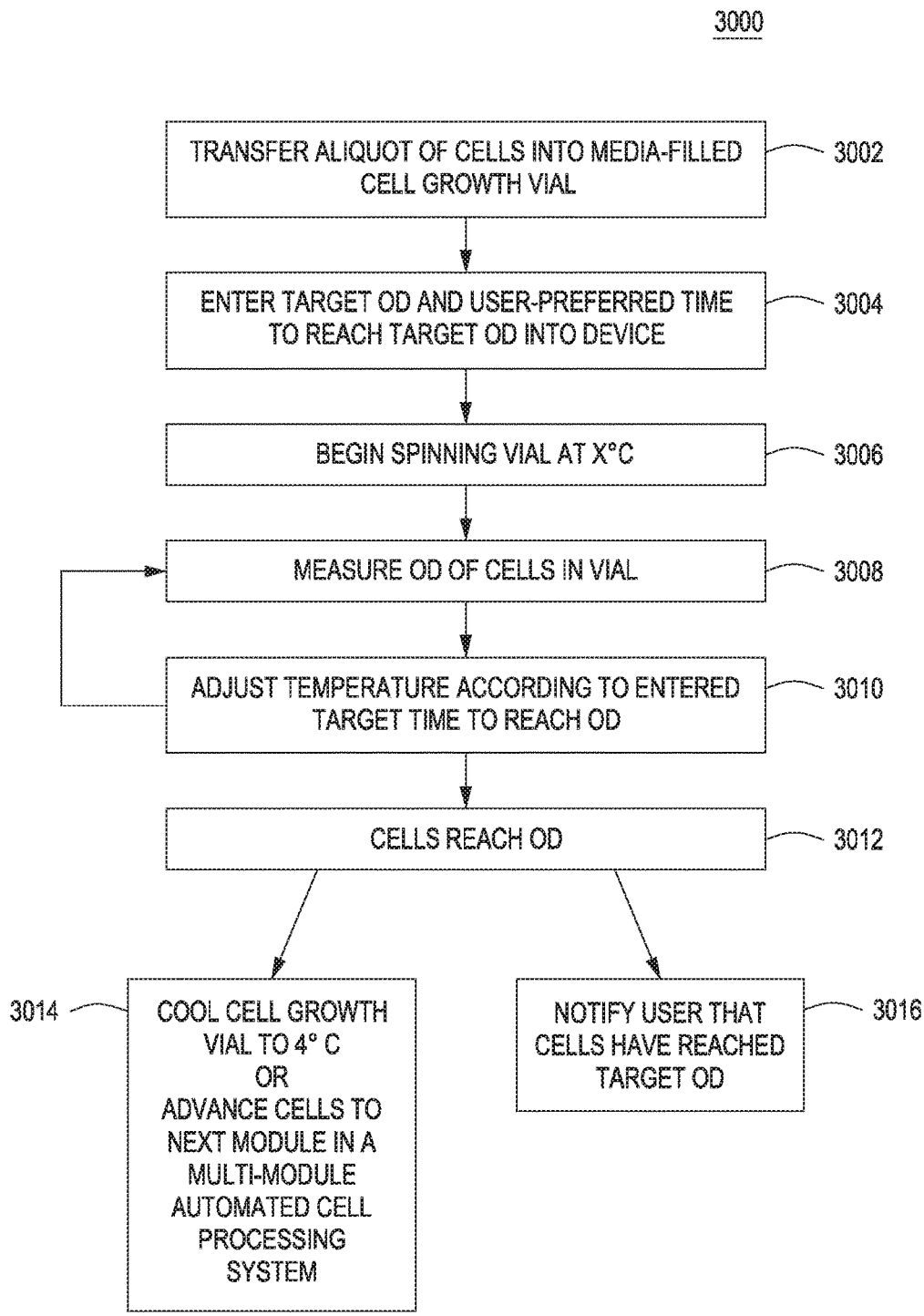
FIG. 2F is a flow chart of one embodiment of a method for using the cell growth device.

FIG. 2F is a block diagram of one method 3000 for using the cell growth device including measuring OD and providing feedback. In a first step of the method, a user transfers an aliquot of cells into a media-filled cell growth vial 3002. The user then specifies via input into a processor a target OD and preferred time that the cell culture reach the target OD 3004. The user can manually enter these parameters, the user may, e.g., choose from a menu of established protocols and parameters, or, in an automated cell processing system, there may be the option of using a barcode or other tag on the rotating growth vial that specifies the protocols and parameters (e.g., the medium contained within the vial, the cell type, the wavelength to read OD, and the desired optical density endpoint) where the barcode is detected by the processor that controls the cell growth device.

At step 3006, the rotation of the rotating cell vial is initiated at a specific temperature. Again, a user may manually specify the temperature and rotation rate of the vial, the user may choose from a menu of established protocols and parameters, or there may be an option of using a barcode or other tag that specifies the protocols and parameters in advance. At step 3008, the OD of the cell culture in the vial is measured. As described above, OD may be measured continuously, may be measured at specific time intervals, or a combination of the two can be used. The cell growth module then adjusts the temperature of the rotating growth vial (and the cell culture) according to the target time requested by the user 3010. The steps of measuring OD 3008 and adjusting the temperature of the cell culture 3010 continue until the cell culture reaches the target OD 3012. At this point, the processor may send a command to the thermal control device to cool the growth vial to, e.g., 4° C. or to freeze the cells. Alternatively, if the cell growth device is part of a system—e.g., one module in a multi-module cell processing system—the processor may advance the cells to a next module 3014. In addition, at step 3016, the processor may notify the user that the cells have reached a target OD, for example, through an application on the user's cell phone or other digital assistant.

Use of the Cell Growth Device in an Automated Multi-Module Cell Processing Instrument As mentioned above, the cell growth device may be used as a stand-alone instrument such as a benchtop instrument, or as a module in an automated multi-module cell processing instrument. One such instrument is an instrument that combines a cell growth module, a cell concentration/buffer exchange module ("cell concentration module"), and a transformation/transfection module ("transformation module"), where a liquid handling system transfers liquids between reagent reservoirs and the three modules automatically without human intervention. FIGS. 3A-3H depict variations of one embodiment of a cell concentration/buffer exchange module that utilizes tangential flow filtration.

The cell concentration module described herein operates using tangential flow filtration (TFF), also known as cross-flow filtration, in which the majority of the feed flows tangentially over the surface of the filter thereby reducing cake (retentate) formation as compared to dead-end filtration, in which the feed flows into the filter. Secondary flows relative to the main feed are also exploited to generate shear forces that prevent filter cake formation and membrane fouling thus maximizing particle recovery, as described below.

Figure 3A:
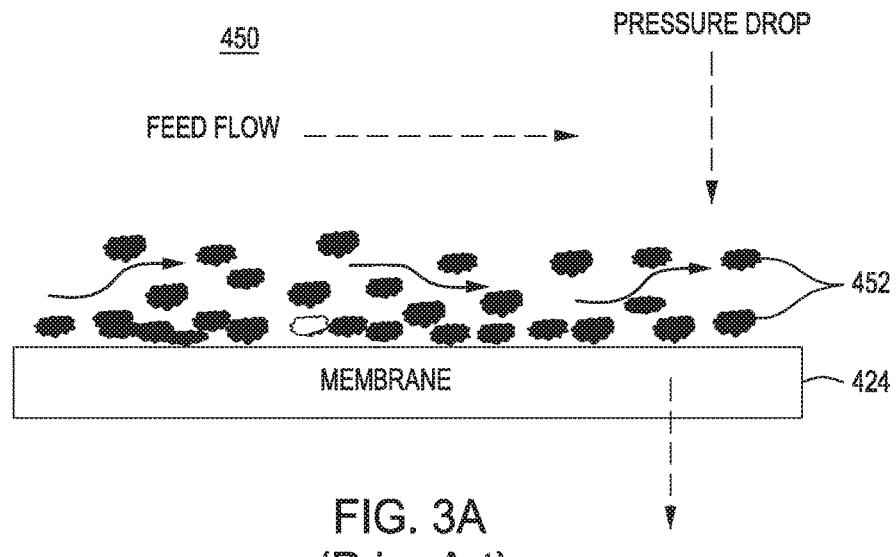
FIG. 3A is a model of tangential flow filtration used in the TFF module presented herein.

The TFF device described herein was designed to take into account two primary design considerations. First, the geometry of the TFF device leads to filtering the cell culture over a large surface area so as to minimize processing time. Second, the design of the TFF device is configured to minimize filter fouling. FIG. 3A is a general model 450 of tangential flow filtration. The TFF device operates using tangential flow filtration, also known as cross-flow filtration. FIG. 3A shows cells flowing over a membrane 424, where the feed flow of the cells 452 in medium or buffer is parallel to the membrane 424. TFF is different from dead-end filtration where both the feed flow and the pressure drop are perpendicular to a membrane or filter.

Figure 3B:
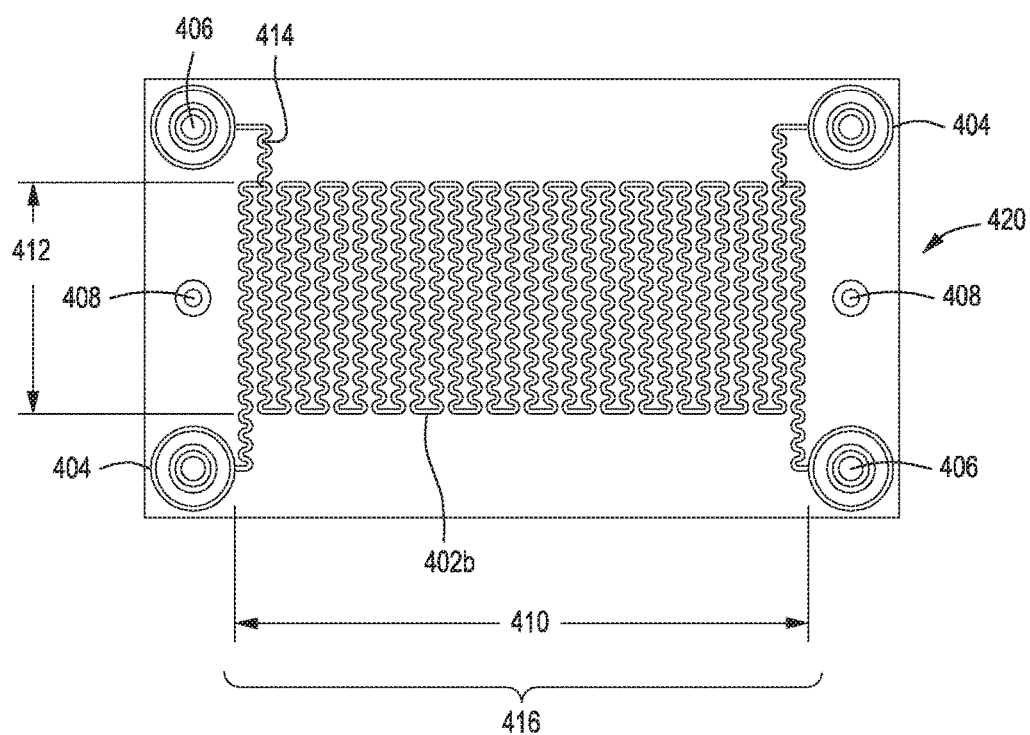
FIG. 3B depicts a top view of a lower member of one embodiment of an exemplary TFF device/module.

FIG. 3B depicts a top view of a lower member 420 of one embodiment of an exemplary TFF device/module providing tangential flow filtration. As can be seen in FIG. 3B, the lower member 420 of the TFF device module comprises a channel structure 416 comprising a flow channel through which a cell culture is flowed. The channel structure 416 comprises a single flow channel 402 that is horizontally bifurcated by a membrane (not shown) through which buffer or medium may flow, but cells cannot. (Note, that the flow channel generally is designated 402, the portion of the flow channel in the upper member 422 of the TFF device is designated 402a, and the portion of the flow channel in the lower member 420 of the TFF device is designated 402b.) This particular embodiment comprises a channel configuration 414, e.g., an undulating serpentine geometry (i.e., the small "wiggles" in the flow channel 402) and a serpentine "zig-zag" pattern where the flow channel 402b crisscrosses the lower member 420 of the TFF device from one end at the left of the device to the other end at the right of the device. The serpentine pattern allows for filtration over a high surface area relative to the device size and total channel volume, while the undulating contribution creates a secondary inertial flow to enable effective membrane regeneration preventing membrane fouling. Although an undulating geometry and serpentine pattern are exemplified here, other channel configurations 414 may be used as long as the flow channel 402 can be bifurcated by a membrane, and, as discussed below, as long as the channel configuration 414 provides for cell flow through the TFF module in alternating directions. Portals 404 and 406 are part of channel structure 416 by operation of the cells passing through flow channel 402. Generally, portals 404 collect cells passing through the flow channel 402 on one side of a membrane (not shown) (the "retentate"), and portals 406 collect the medium ("filtrate" or "permeate") passing through the flow channel 402 on the opposite side of the membrane (not shown). In this embodiment, recesses 408 accommodate screws or other fasteners (not shown) that allow the components of the TFF device to be secured to one another.

The length 410 and width 412 of the channel structure 416 may vary depending on the volume of the cell culture to be grown and the optical density of the cell culture to be concentrated. The length 410 of the channel structure 416 typically is from 1 mm to 300 mm, or from 50 mm to 250 mm, or from 60 mm to 200 mm, or from 70 mm to 150 mm, or from 80 mm to 100 mm. The width of the channel structure 416 typically is from 1 mm to 120 mm, or from 20 mm to 100 mm, or from 30 mm to 80 mm, or from 40 mm to 70 mm, or from 50 mm to 60 mm. The cross-section configuration of the flow channel 402 may be round, elliptical, oval, square, rectangular, trapezoidal, or irregular. If square, rectangular, or another shape with generally straight sides, the cross section may be from about 10 μm to 1000 μm wide, or from 200 μm to 800 μm wide, or from 300 μm to 700 μm wide, or from 400 μm to 600 μm wide; and from about 10 μm to 1000 μm high, or from 200 μm to 800 μm high, or from 300 μm to 700 μm high, or from 400 μm to 600 μm high. If the cross section of the flow channel 102 is generally round, oval or elliptical, the radius of the channel may be from about 50 μm to 1000 μm in hydraulic radius, or from 5 μm to 800 μm in hydraulic radius, or from 200 μm to 700 μm in hydraulic radius, or from 300 μm to 600 μm wide in hydraulic radius, or from about 200 to 500 μm in hydraulic radius.

When looking at the top view of lower member 420 of the TFF device/module of FIG. 3B, note that there are two retentate portals 404 and two filtrate portals 406, where there is one of each type of portal at both ends (e.g., the narrow edge) of the TFF device/module 400. In other embodiments, retentate and filtrate portals can be on the same surface of the same member (e.g., upper 422 or lower member 420), or they can be arranged on the side surfaces of the assembly. Unlike other tangential flow filtration devices that operate continuously, the TFF device/module described herein uses an alternating method for concentrating cells. The overall work flow for cell concentration using the TFF device/module involves flowing a cell culture or cell sample tangentially through the channel structure 416. The membrane bifurcating the flow channels 402 retains the cells on one side of the membrane and allows unwanted medium or buffer to flow across the membrane into the filtrate side (e.g, lower member 420) of the device. In this process, a fixed volume of cells in medium or buffer is driven through the device until the cell sample is collected into one of the retentate portals 404, and the medium/buffer that has passed through the membrane is collected through one or both of the filtrate portals 406. All types of prokaryotic and eukaryotic cells—both adherent and non-adherent cells—can be concentrated in the TFF device. Adherent cells may be grown on beads or other cell scaffolds suspended in medium in the rotating growth vial, then passed through the TFF device.

In the cell concentration process, passing the cell sample through the TFF device and collecting the cells in one of the retentate portals 404 while collecting the medium in one of the filtrate portals 406 is considered "one pass" of the cell sample. The transfer between retentate reservoirs "flips" the culture. The retentate and filtrate portals collecting the cells and medium, respectively, for a given pass reside on the same end of TFF device/module 400 with fluidic connections arranged so that there are two distinct flow layers (not shown) for the retentate and filtrate sides, but if the retentate portal 404 resides on the upper member 422 of the TFF device/module 400 (that is, the cells are driven through the flow channel 402a (not shown) above the membrane and the filtrate (medium) passes to the portion of the flow channel 402b below the membrane), the filtrate portal 406 will reside on the lower member of device/module 400 and vice versa (that is, if the cell sample is driven through the flow channel 402b below the membrane, the filtrate (medium) passes to the portion of the flow channel 402a above the membrane). This configuration can be seen more clearly in FIGS. 3C-3D, where the retentate flows 460 from the retentate portals 404 and the filtrate flows 470 from the filtrate portals 406.

At the conclusion of a "pass", the cell sample is collected by passing through the retentate portal 404 and into the retentate reservoir (not shown). To initiate another "pass", the cell sample is passed again through the TFF device, this time in a flow direction that is reversed from the first pass. The cell sample is collected by passing through the retentate portal 404 and into retentate reservoir (not shown) on the opposite end of the device/module from the retentate portal 404 that was used to collect cells during the first pass. Likewise, the medium/buffer that passes through the membrane on the second pass is collected through the filtrate portal 406 on the opposite end of the device/module from the filtrate portal 406 that was used to collect the filtrate during the first pass, or through both portals. This alternating process of passing the retentate (the concentrated cell sample) through the device/module is repeated until the cells have been concentrated to a desired volume, and both filtrate portals can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell concentration may (and typically do) take place simultaneously.

Figure 3C:
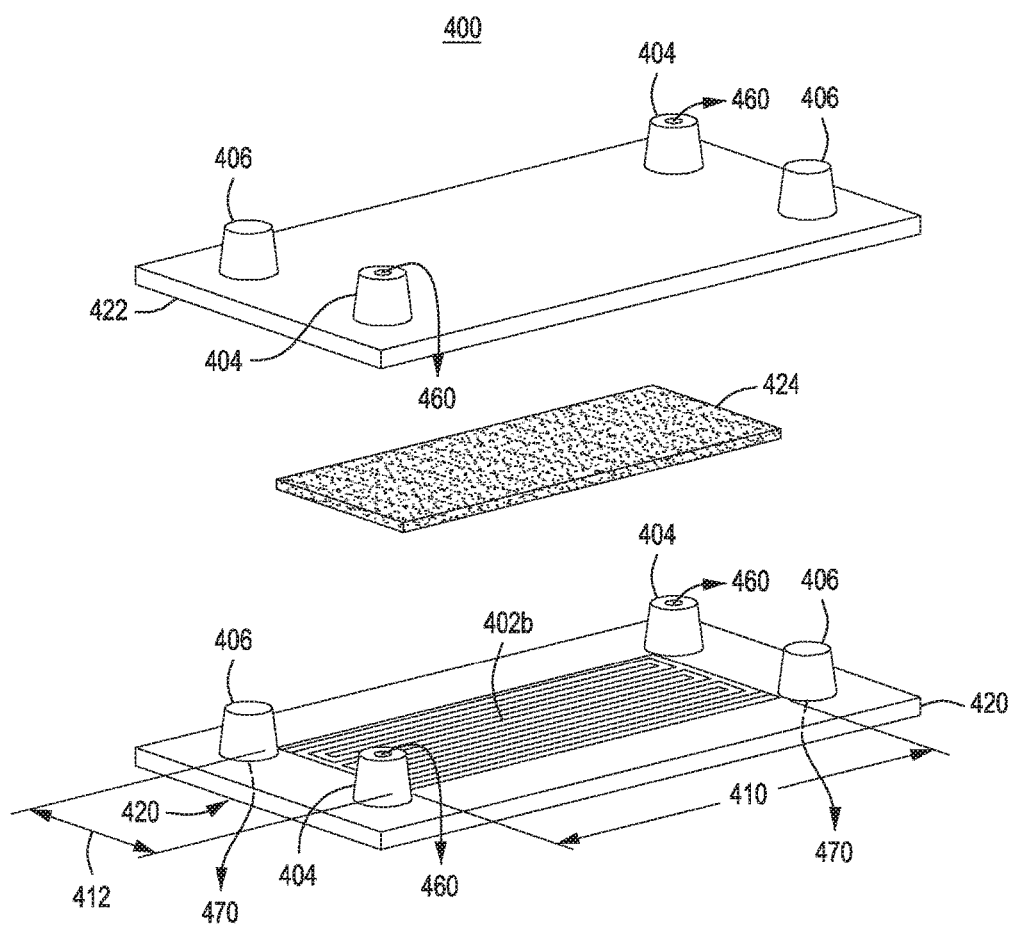
FIG. 3C depicts a top view of upper and lower members and a membrane of an exemplary TFF module.

FIG. 3C depicts a top view of upper (422) and lower (420) members of an exemplary TFF module 400. Again, portals 404 and 406 are seen. As noted above, recesses—such as the recesses 408 seen in FIG. 3B—provide a means to secure the components (upper member 422, lower member 420, and membrane 424) of the TFF device/membrane 400 to one another during operation via, e.g., screws or other like fasteners. However, in alternative embodiments, an adhesive—such as a pressure sensitive adhesive—or ultrasonic welding, or solvent bonding, may be used to couple the upper member 422, lower member 420, and membrane 424 together. Indeed, one of ordinary skill in the art given the guidance of the present disclosure can find yet other configurations for coupling the components of the TFF device 400, such as e.g., clamps; mated fittings disposed on the upper (422) and lower (420) members; combination of adhesives, welding, solvent bonding, and mated fittings; and other such fasteners and couplings.

Note that in FIG. 3C there is one retentate portal 404 and one filtrate portal 406 on each "end" (e.g., the narrow edges) of the TFF device/module 400. The retentate 404 and filtrate 406 portals on the left side of the TFF device/module 400 will collect cells (flow path at 460) and medium (flow path at 470), respectively, for the same pass. Likewise, the retentate 404 and filtrate 406 portals on the right side of the TFF device/module 400 will collect cells (flow path at 460) and medium (flow path at 470), respectively, for the same pass. In this embodiment, the retentate is collected from portals 404 on the top surface of the TFF device, and filtrate is collected from portals 406 on the bottom surface of the device. The cells are maintained in the TFF flow channel 402a above the membrane 424, while the filtrate (medium) flows through membrane 424 and then through filtrate portals 406; thus, the top/retentate portals 404 and bottom/filtrate portals 406 configuration is practical. It should be recognized, however, that other configurations of retentate 404 and filtrate 406 portals may be implemented such as positioning both the retentate 404 and filtrate 406 portals on the side surface (as opposed to the top and bottom surfaces) of the TFF device 400. In FIG. 3C, the flow channel 402b can be seen on the lower member 420 of the TFF device 400. However, in other embodiments, retentate 404 and filtrate 406 portals can reside on the same surface of the TFF device.

Also seen in FIG. 3C is membrane or filter 424. Filters or membranes appropriate for use in the TFF device/module 400 are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 5 µm. Indeed, the pore sizes useful in the TFF device/module 400 include filters 424 with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters 424 may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching. The TFF device 400 shown in FIGS. 3C and 3D does not show a seat in the upper 422 and lower 420 members where the filter 424 can be seated or secured (for example, a seat half the thickness of the filter 424 in each of upper 422 and lower 420 members); however, such a seat is contemplated in some embodiments.

Figure 3E:
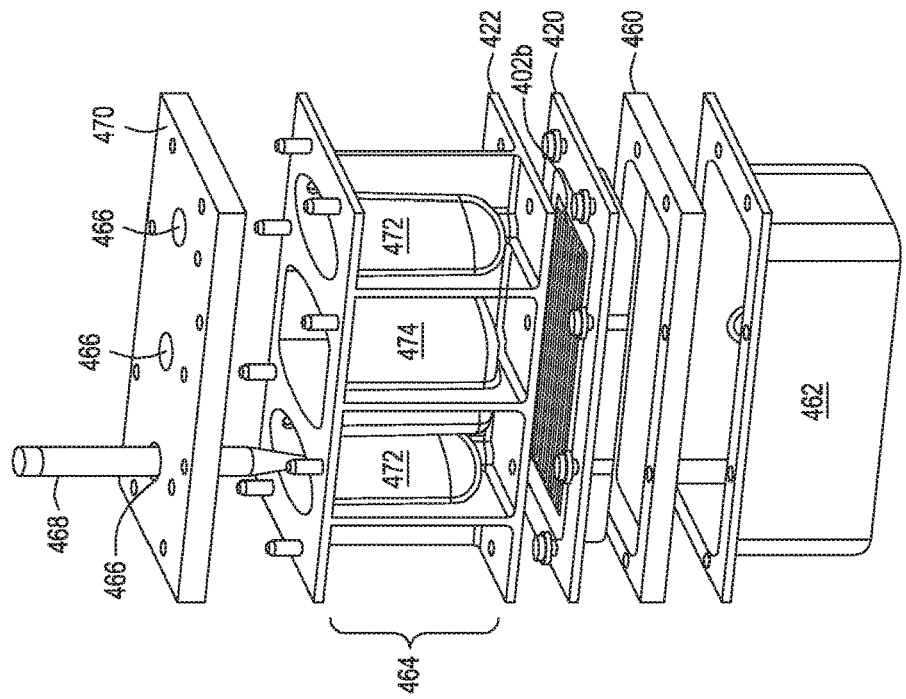
FIGS. 3E-3H depict various views of an embodiment of a TFF module having fluidically coupled reservoirs for retentate, filtrate, and exchange buffer.
Figure 3D:
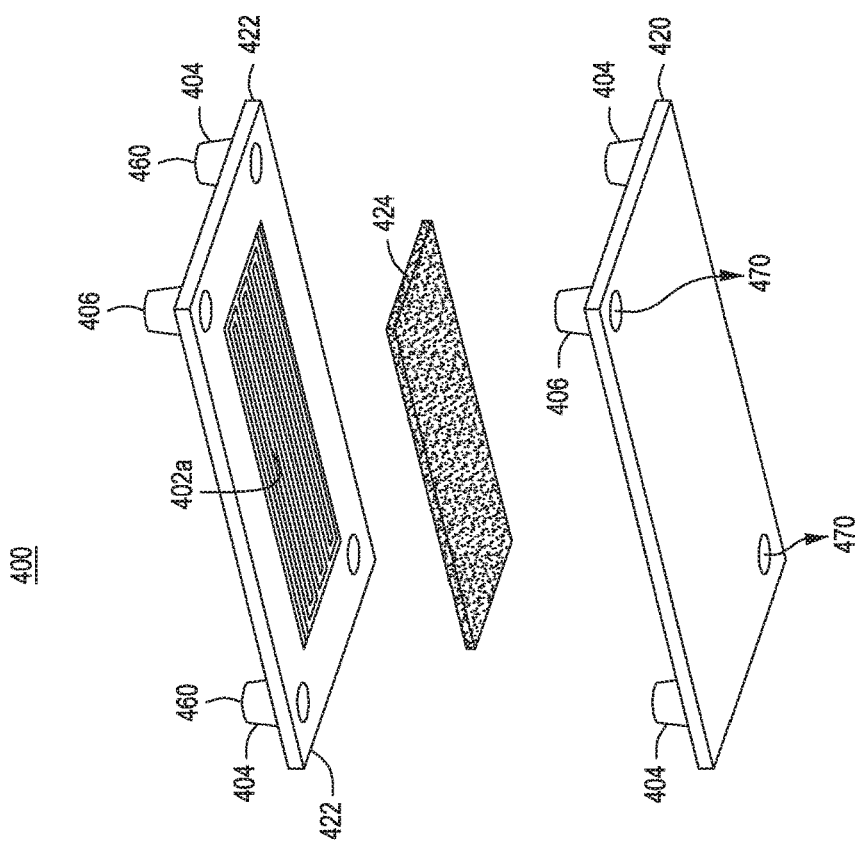
FIG. 3D depicts a bottom view of upper and lower members and a membrane of an exemplary TFF module.

FIG. 3D depicts a bottom view of upper and lower components of the exemplary TFF module shown in FIG. 3C. FIG. 3D depicts a bottom view of upper (422) and lower (420) members of an exemplary TFF module 400. Again portals 404 and 406 are seen. Note again that there is one retentate portal 404 and one filtrate portal 406 on each end of the upper member 422 and lower member 420 of the TFF device/module 400. On the left side of the TFF device 400, the retentate portals 404 will collect cells (flow path at 460) and the filtrate portals 406 will collect medium (flow path at 470), respectively, for the same pass. Likewise, on the right side of the TFF device 400, the retentate portals 404 will collect cells (flow path at 460) and the filtrate portals 406 will collect medium (flow path at 470), respectively, for the same pass. In FIG. 3D, the flow channel 402a can be seen on the upper member 422 of the TFF device 400. Thus, looking at FIGS. 3C and 3D, note that there is a flow channel 402 in both the upper member 422 (flow channel 402a) and lower member 422 (flow channel 402b) with a membrane 424 between the upper 422 and lower 420 members. The flow channels 402a and 402b of the upper 422 and lower 420 members mate to create the flow channel 402 with the membrane 424 positioned horizontally between the upper and lower members of the TFF device/module thereby bifurcating the flow channel 402.

Buffer exchange during cell concentration and/or rendering the cells competent is performed on the TFF device/module 400 by adding a desired buffer to the cells concentrated to a desired volume; for example, after the cells have been concentrated at least 20-fold, 30-fold, 40-fold, 50-fold, 60-fold, 70-fold, 80-fold, 90-fold, 100-fold, 150-fold, 200-fold or more. A desired exchange medium or exchange buffer is added to the cells either by addition to the retentate reservoir (not shown) or through the membrane 424 from the filtrate side (e.g., to cells in retentate reservoir) and the process of passing the cells through the TFF device 400 is repeated until the cells have been concentrated to a desired volume in the exchange medium or buffer. This process can be repeated any number of desired times so as to achieve a desired level of exchange of the buffer and a desired volume of cells. As described in the Example I, the exchange buffer may comprise, e.g., glycerol or sorbitol thereby rendering the cells competent for transformation in addition to decreasing the overall volume of the cell sample.

The TFF device 400 may be fabricated from any robust material in which flow channels may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module 400 is disposable, preferably it is made of plastic. In some embodiments, the material used to fabricate the TFF device/module 400 is thermally-conductive so that the cell culture may be heated or cooled to a desired temperature. In certain embodiments, the TFF device 400 is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to these mass production techniques.

FIG. 3E depicts an exploded perspective view of one exemplary embodiment of a TFF module having fluidically coupled reservoirs for retentate, filtrate, and exchange buffer. In this configuration, 470 is the top or cover of the TFF device, having three ports 466, where there is a pipette tip 468 disposed in the left-most port 466. The top 470 of the TFF device is, in operation, coupled with a combined reservoir and upper member structure 464. Combined reservoir and upper member structure 464 comprises a top surface that, in operation, is adjacent the top or cover 470 of the TFF device, a bottom surface which comprises the upper member 422 of the TFF device, where the upper member 422 of the TFF device defines the upper portion of the tangential flow channel (not shown). Combined reservoir and upper member structure 464 comprises two retentate reservoirs 472 and buffer or medium reservoir 474. The retentate reservoirs 472 are fluidically coupled to the upper portion of the flow channel, and the buffer or medium reservoir 474 is fluidically coupled to the retentate reservoirs 472. Also seen in this exploded view of the TFF device is lower member 420 which, as described previously, comprises on its top surface the lower portion of the tangential flow channel 402*b* (seen on the top surface of lower member 420), where the upper and lower portions of the flow channel 402 of the upper member 422 and lower member 420, respectively, when coupled mate to form a single flow channel 402 (the membrane that is interposed between the upper member 422 and lower member 420 in operation is not shown). Beneath lower member 420 is gasket 460, which in operation is interposed between lower member 420 and a filtrate (or permeate) reservoir 462. In operation, top 470, combined reservoir and upper member structure 464, membrane (not shown), lower member 420, gasket 460, and filtrate reservoir 462 are coupled and secured together to be fluid- and air-tight. In FIG. 3E, fasteners are shown that can be used to couple the various structures (top 470, combined reservoir and upper member structure 464, membrane (not shown), lower member 420, gasket 460, and filtrate reservoir 462) together. However, as an alternative to screws or other like fasteners, the various structures of the TFF device can be coupled using an adhesive, such as a pressure sensitive adhesive; ultrasonic welding; or solvent bonding. Further, a combination of fasteners, adhesives, and/or welding types may be employed to couple the various structures of the TFF device. One of ordinary skill in the art given the guidance of the present disclosure could find yet other configurations for coupling the components of the TFF device, such as, e.g., clamps, mated fittings, and other such fasteners.

Figure 3F:
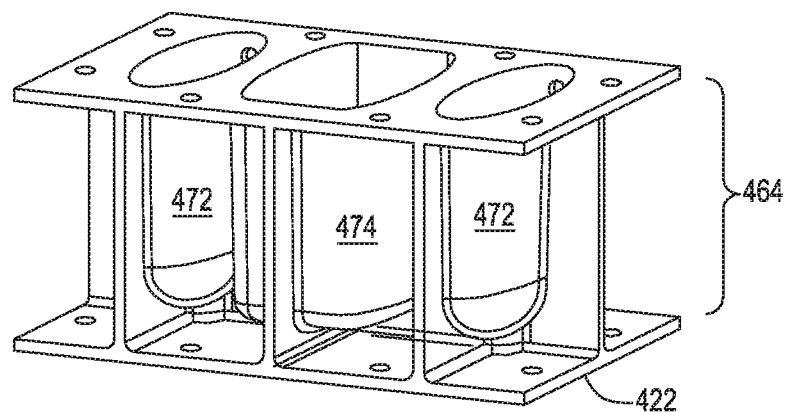
Figure 3G:
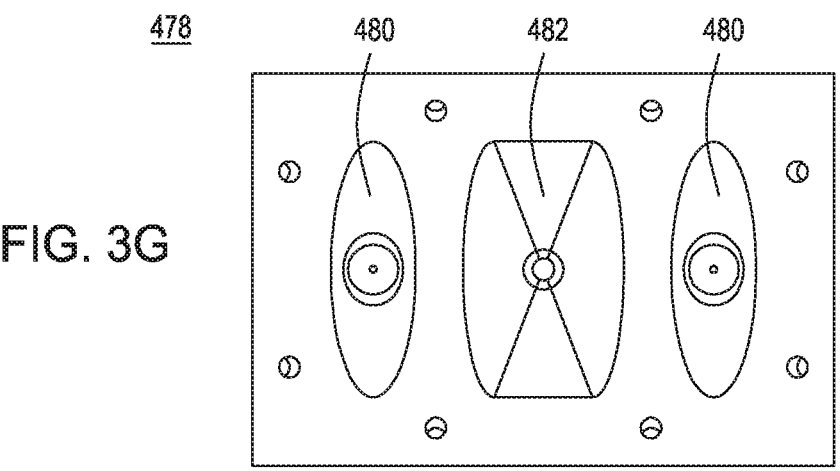
Figure 3H:
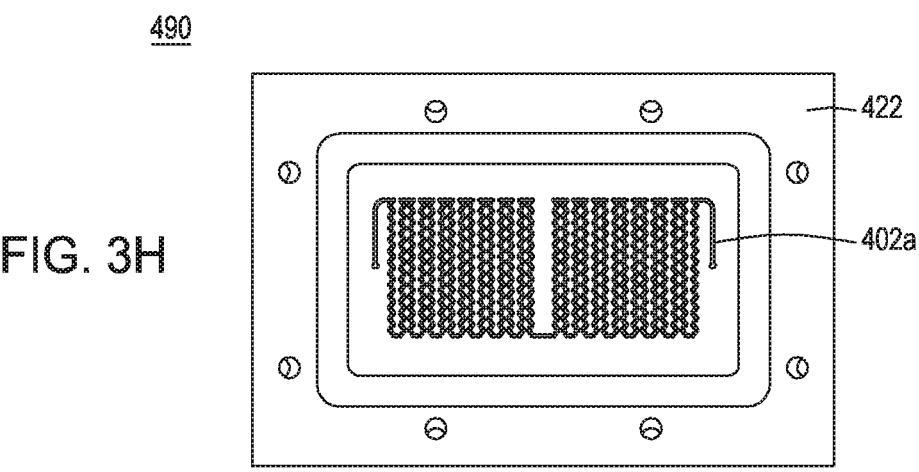

FIG. 3F depicts combined reservoir and upper member structure 464, comprising two retentate reservoirs 472 and buffer or medium reservoir 474, as well as upper member 422, which is disposed on the bottom of combined reservoir and upper member structure 464. Upper member 422 of the TFF device defines the upper portion of the tangential flow channel (not shown) disposed on the bottom surface of the combined reservoir and upper member structure 464. FIG. 3G is a top-down view of the upper surface 478 of combined reservoir and upper member structure 464, depicting the top 480 of retentate reservoirs 472 and the top 482 of buffer or medium reservoir 474. The retentate reservoirs 472 are fluidically coupled to the upper portion of the flow channel (not shown), and the buffer or medium reservoir 474 is fluidically coupled to the retentate reservoirs 472. FIG. 3H is a bottom-up view of the lower surface 490 of combined reservoir and upper member structure 464, showing the upper member 422 with the upper portion of the tangential flow channel 402*a* disposed on the bottom surface of upper member 422. The flow channel 402*a* disposed on the bottom surface of upper member 422 in operation is mated to the bottom portion of the tangential flow channel 402*b* disposed on the top surface of the lower member 420 (not shown in this view, but see FIG. 3E), where the upper and lower portions of the flow channels 402*a* and 402*b*, respectively, mate to form a single flow channel 402 with a membrane or filter (not shown) interposed between the upper 402*a* and lower 402*b* portions of the flow channel.

Figure 4A:
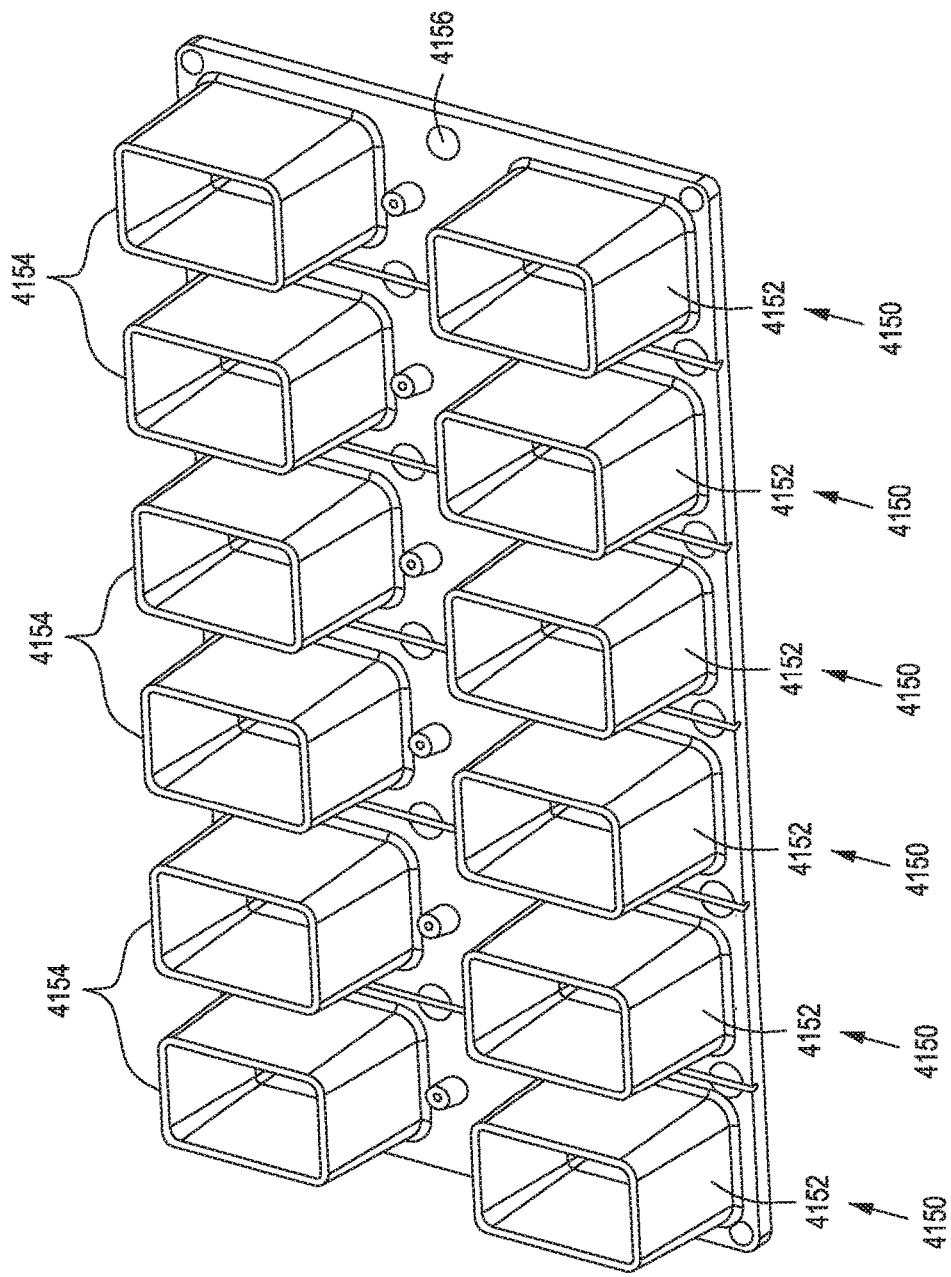
FIGS. 4A and 4B are top perspective and bottom perspective views, respectively, of flow-through electroporation devices (here, there are six such devices co-joined).
Figure 4B:
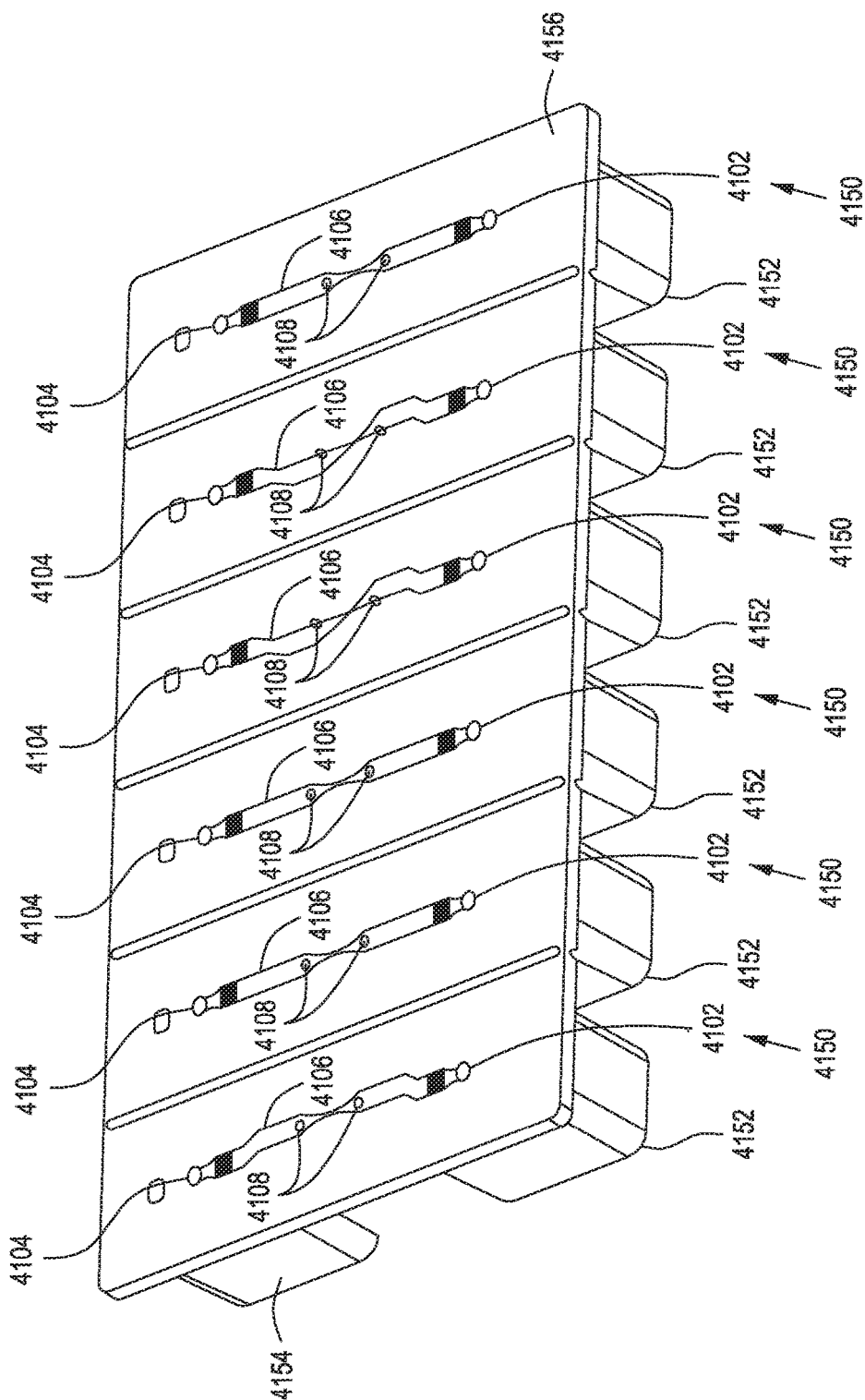

Turning to the third module of the three-module cell growth, cell concentration, and cell transformation instrument, FIGS. 4A-4E depict variations on one embodiment of a cell transformation module (in this case, a flow-through electroporation device) that may be included in a cell growth/concentration/transformation instrument. FIGS. 4A and 4B are top perspective and bottom perspective views, respectively, of six co-joined flow-through electroporation devices 4150. FIG. 4A depicts six flow-through electroporation units 4150 arranged on a single substrate 4156. Each of the six flow-through electroporation units 4150 have inlet wells 4152 that define cell sample inlets and outlet wells 4154 that define cell sample outlets. FIG. 4B is a bottom perspective view of the six co-joined flow-through electroporation devices of FIG. 4A also depicting six flow-through electroporation units 4150 arranged on a single substrate 4156. Six inlet wells 4152 can be seen, one for each flow-through electroporation unit 4150, and one outlet well 4154 can be seen (the outlet well of the left-most flow-through electroporation unit 4150). Additionally seen in FIG. 4B are an inlet 4102, outlet 4104, flow channel 4106 and two electrodes 4108 on either side of a constriction in flow channel 4106 in each flow-through electroporation unit 4150. Once the six flow-through electroporation units 4150 are fabricated, they can be separated from one another (e.g., "snapped apart") and used one at a time, or alternatively in embodiments where two or more flow-through electroporation units 4150 can be used in parallel without separation.

The flow-through electroporation devices 4150 achieve high efficiency cell electroporation with low toxicity. The flow-through electroporation devices 4150 of the disclosure allow for particularly easy integration with robotic liquid handling instrumentation that is typically used in automated systems such as air displacement pipettors. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

Generally speaking, microfluidic electroporation—using cell suspension volumes of less than approximately 10 ml and as low as 1 µl—allows more precise control over a transfection or transformation process and permits flexible integration with other cell processing tools compared to bench-scale electroporation devices. Microfluidic electroporation thus provides unique advantages for, e.g., single cell transformation, processing and analysis; multi-unit electroporation device configurations; and integrated, automatic, multi-module cell processing and analysis.

In specific embodiments of the flow-through electroporation devices 4150 of the disclosure, the toxicity level of the transformation results in greater than 10% viable cells after electroporation, preferably greater than 15%, 20%, 25%, 30%, 35%, 40%, 45%, 50%, 55%, 60%, 70%, 75%, 80%, 85%, 90%, or even 95% viable cells following transformation, depending on the cell type and the nucleic acids being introduced into the cells.

The flow-through electroporation device 4150 described in relation to FIGS. 4A-4E comprises a housing with an electroporation chamber, a first electrode and a second electrode configured to engage with an electric pulse generator, by which electrical contacts engage with the electrodes of the electroporation device 4150. In certain embodiments, the electroporation devices are autoclavable and/or disposable, and may be packaged with reagents in a reagent cartridge. The electroporation device 4150 may be configured to electroporate cell sample volumes between 1 µl to 2 ml, 10 µl to 1 ml, 25 µl to 750 µl, or 50 µl to 500 µl. The cells that may be electroporated with the disclosed electroporation devices 4150 include mammalian cells (including human cells), plant cells, yeasts, other eukaryotic cells, bacteria, archaea, and other cell types.

Figure 4C:
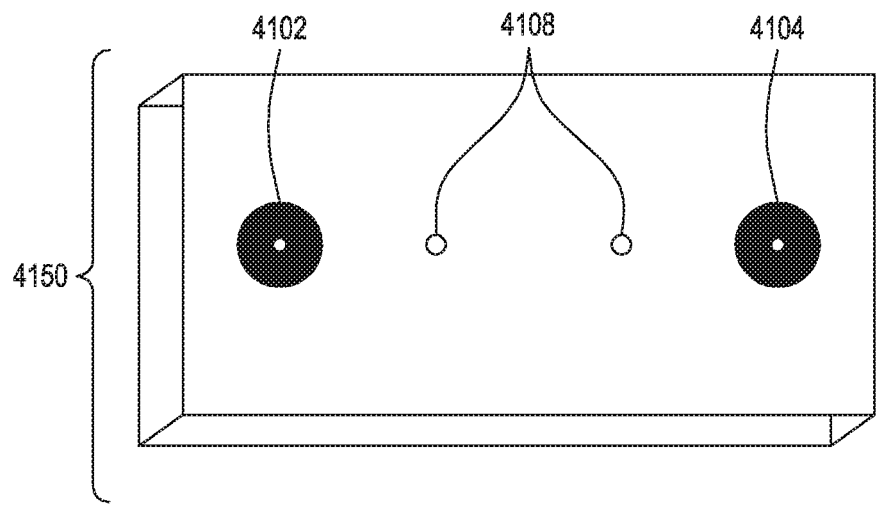
FIG. 4C is a top view of one embodiment of an exemplary flow-through electroporation device.
Figure 4D:
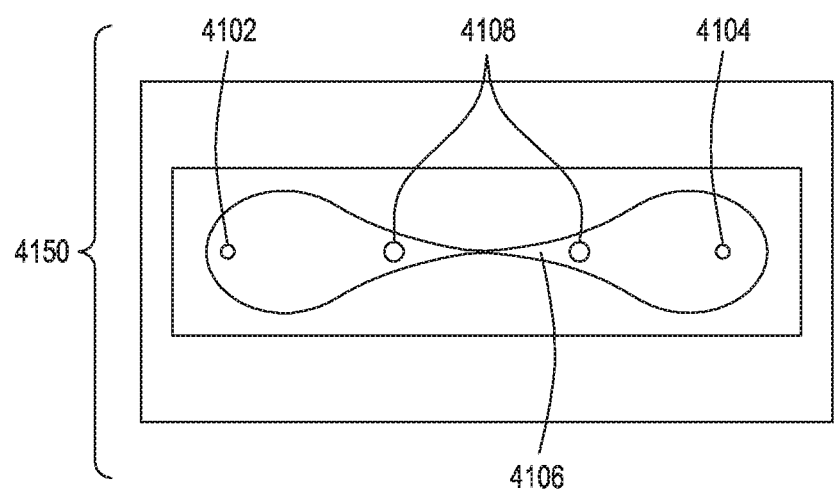
FIG. 4D depicts a top view of a cross section of the electroporation device of FIG. 4C.
Figure 4E:
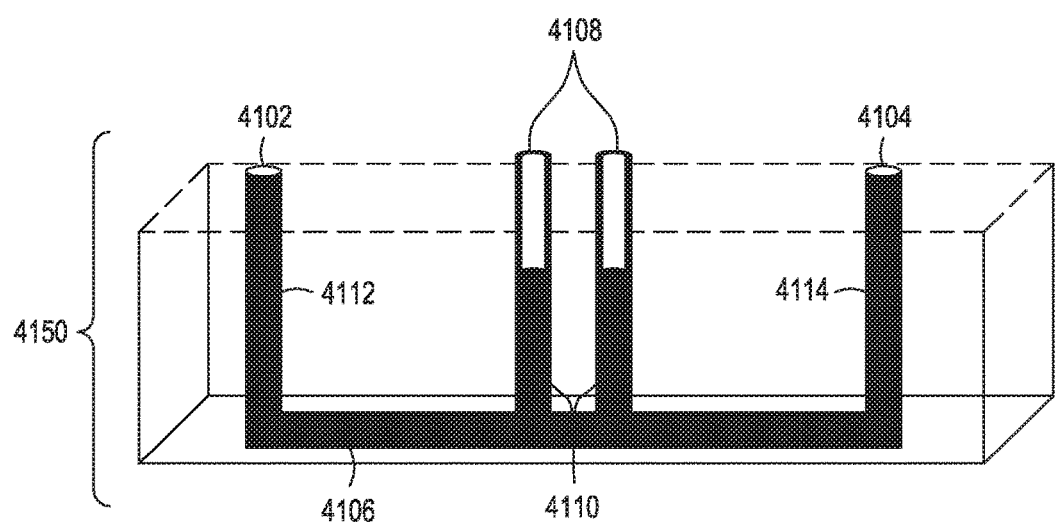
FIG. 4E is a side view cross section of a lower portion of the electroporation devices of FIGS. 4C and 4D.

In one exemplary embodiment, FIG. 4C depicts a top view of a flow-through electroporation device 4150 having an inlet 4102 for introduction of cells and an exogenous reagent to be electroporated into the cells ("cell sample") and an outlet 4104 for the cell sample following electroporation. Electrodes 4108 are introduced through electrode channels (not shown) in the device. FIG. 4D shows a cutaway view from the top of flow-through electroporation device 4150, with the inlet 4102, outlet 4104, and electrodes 4108 positioned with respect to a constriction in flow channel 4106. A side cutaway view of a lower portion of flow-through electroporation device 4150 in FIG. 4E illustrates that electrodes 4108 in this embodiment are positioned in electrode channels 4110 and perpendicular to flow channel 4106 such that the cell sample flows from the inlet channel 4112 through the flow channel 4106 to the outlet channel 4114, and in the process the cell sample flows into the electrode channels 4110 to be in contact with electrodes 4108. In this aspect, the inlet channel 4112, outlet channel 4114 and electrode channels 4110 all originate from the top planar side of the device; however, the flow-through electroporation architecture depicted in FIGS. 4C-4E is but one architecture useful with the reagent cartridges described herein. Additional electrode architectures are described, e.g., in U.S. Ser. No. 16/147,120, filed 24 Sep. 2018; Ser. No. 16/147,865, filed 30 Sep. 2018; and Ser. No. 16/147,871, filed 30 Sep. 2018.

In addition to the cell growth/concentration/transformation instrument described above with the three linked modules, additional modules may be included in a multi-module cell processing instrument, such as that depicted in FIG. 5. FIG. 5 depicts an exemplary automated multi-module cell processing instrument 5000 comprising a TFF module 5022 as described above, a flow-through electroporation device 5030 as described above, as well as additional exemplary modules. Illustrated is a gantry 5002, providing an automated mechanical motion system (actuator) (not shown) that supplies XYZ axis motion control to, e.g., modules of the automated multi-module cell processing instrument 5000, including, e.g., an air displacement pipette (not shown). In some automated multi-module cell processing instruments, the air displacement pipettor is moved by a gantry and the various modules and reagent cartridges remain stationary; however, in other embodiments, the pipetting system may stay stationary while the various modules are moved. Also included in the automated multi-module cell processing instrument 5000 is wash or reagent cartridge 5004, comprising reservoirs 5006 and large and small tubes or reservoirs 5006. Wash or reagent cartridge 5004 may be configured to accommodate large tubes, for example, wash solutions, or solutions that are used often throughout an iterative process. In one example, wash or reagent cartridge 5004 may be configured to remain in place when two or more reagent cartridges 5010 are sequentially used and replaced. Although reagent cartridge 5010 and wash or reagent cartridge 5004 are shown in FIG. 5 as separate cartridges, the contents of wash cartridge 5004 may be incorporated into reagent cartridge 5010. Reagent cartridge 5004 comprises 18 reagent vials 5012.

The exemplary automated multi-module cell processing instrument 5000 of FIG. 5 further comprises a cell growth module 5034. In the embodiment illustrated in FIG. 5, the cell growth module 5034 comprises two rotating growth vials 5018, 5020 (described in detail with relation to FIGS. 1A-1E) as well as a TFF growth cell module 5034. There may be additional cell concentration devices in addition to the cell concentration capabilities of the TFF module 5034, for, e.g., cell preparation or concentration in different cell processes. Examples of cell concentration devices that do not utilize tangential flow include those described in U.S. Ser. No. 16/253,564, filed 22 Jan. 2019. Also illustrated as part of the automated multi-module cell processing instrument 5000 of FIG. 5 are pipet tips 5028, for use with air displacement pipettor (not shown), a waste repository 5026, an optional nucleic acid assembly/desalting module 5014 comprising a reaction chamber or tube reservoir (not shown) and further comprising a magnet 5016 to allow for purification of nucleic acids using, e.g., magnetic solid phase reversible immobilization (SPRI) beads (Applied Biological Materials Inc., Richmond, BC).

Use of the Cell Growth Device

Figure 6:
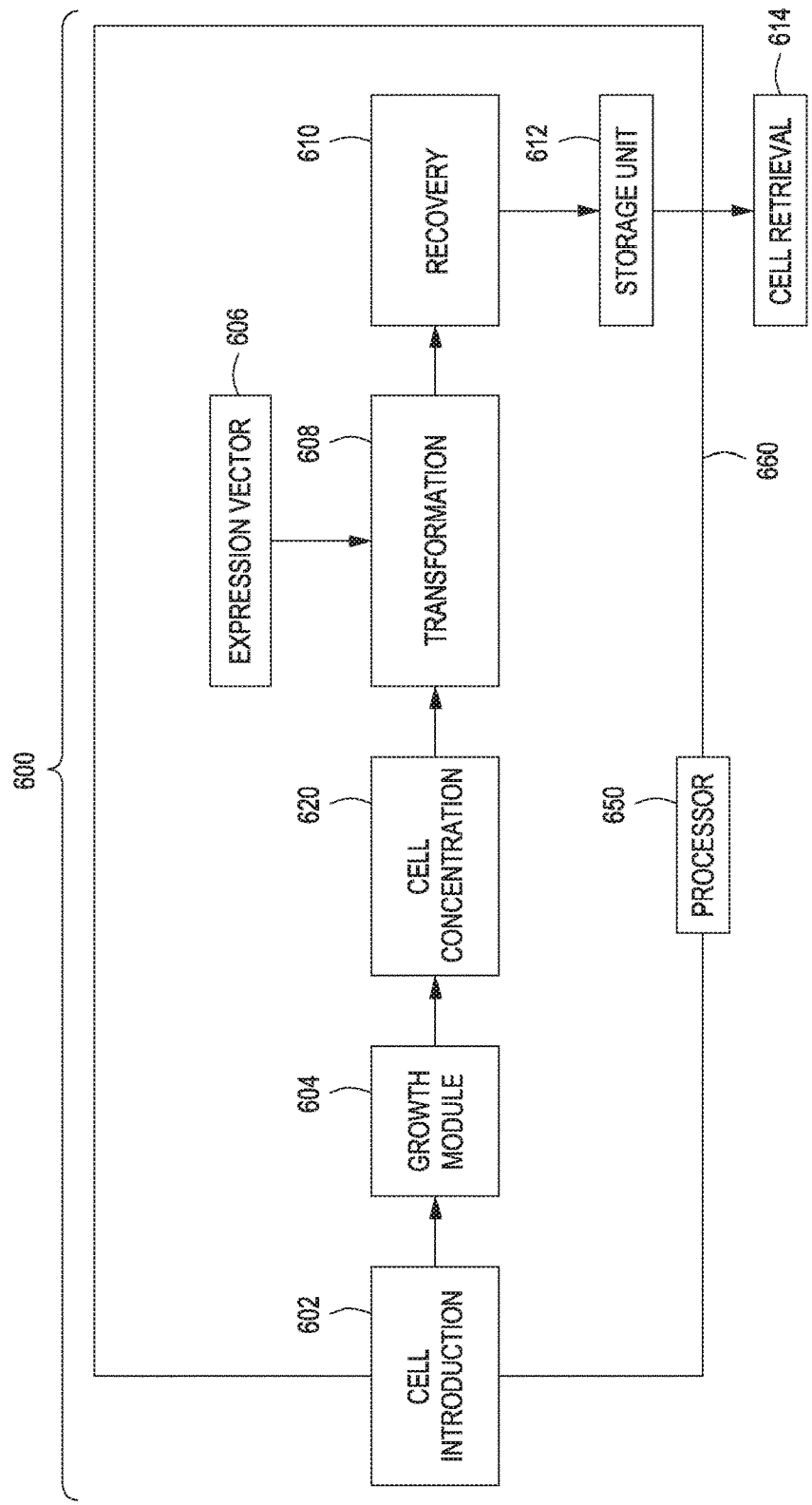
FIG. 6 is a simplified block diagram of one embodiment of an exemplary automated multi-module cell processing instrument that includes a cell growth module.

A general embodiment of a multi-module cell processing system is shown in FIG. 6. In some embodiments, the cell processing system 600 may include a housing 660, a receptacle for introducing cells to be transformed or transfected 602, and a growth module (a cell growth device) 604. The cells to be transformed are transferred to the growth module 604 to be cultured until the cells hit a target OD. Once the cells hit the target OD, the growth module 604 may cool or freeze the cells for later processing or transfer the cells to a cell concentration module 620. The cell concentration module 620 comprises the TFF device to generate concentrated electrocompetent cells. In one example, 20 ml of cells+ growth media is concentrated to 400 µl cells in 10% glycerol. Once the electrocompetent cells have been concentrated, the cells are transferred to a transformation module 608, such as the flow-through electroporation device 4150 above, to be transformed with a desired nucleic acid. In addition to the receptacle for receiving and introducing cells into the TFF device 602, the multi-module cell processing system 600 includes an expression vector receptacle 606 for receiving nucleic acids (e.g., expression or editing vectors) to be transformed or transfected into the cells. The vectors are transferred to the transformation module 608 which already contains the concentrated electrocompetent cells grown to the specified OD, where the nucleic acids are introduced into the cells. Following transformation, the cells are transferred into, e.g., a recovery module 610. Here, the cells are allowed to recover from the transformation process, such as an electroporation procedure described above. In addition or alternatively, the recovery module 610 may also be used as a selection module, where the cells that have been transformed are selected by, e.g., antibiotics added to the medium in the recovery module.

In some embodiments, after recovery the cells are transferred to a storage module 612 to be stored at, e.g., 4° C. or frozen. The cells can then be retrieved from a retrieval module 614 and used for protein expression or further studies off-line. The automated multi-module cell processing system 600 is controlled by a processor 650 configured to operate the instrument based on user input. The processor 650 may control the timing, duration, temperature, and other operations (including, e.g., dispensing reagents) of the various modules of the cell processing system 600. The processor 650 may be programmed with standard protocol parameters from which a user may select; alternatively, a user may select one or all parameters manually. The processor 650 may control the wavelength at which OD is read in the cell growth module 604, the target OD to which the cells are grown, and the target time at which the cells will reach the target OD. In addition, the processor 650 may notify the user (e.g., via an application to a smart phone or other device) that the cells have reached the target OD as well as update the user as to the progress of the cells in the cell growth module 604 and the other modules in the multi-module system 600. Further, it should be appreciated that a stand-alone instrument may include two to many cell growth devices (and cells concentration and/or transformation devices) in parallel.

The multi-module cell processing systems 600 that comprise the cell growth module 604 often comprise a cell concentration module 620 (as described above) and a transformation module 608 (as described above). Again, the cell concentration module 620 is configured to render electrocompetent and concentrate the cells that have been grown to a target OD to an appropriate volume for cell transformation. For example, a 20 ml sample of cells in growth media is rendered electrocompetent and concentrated to, e.g., 400 µl of cells. Concentration of the cells may be accomplished by, e.g., the tangential flow filter (TFF) device described above, or by a centrifuge or filter, by techniques known to those of ordinary skill in the art. Once the cells have been concentrated and rendered electrocompetent, the cells may be transferred to the transformation module 608.

The transformation module 608 may be configured to provide cell transformation or transfection techniques used in molecular biology. The reagents and processing conditions for standard, routinely-used transformation methods may be programmed into a processor and may be selected from, e.g., a menu by a user. Alternatively, a user may manually select reagents and processing conditions. Reagents may reside within the transformation module 608 in bulk or may be provided with the cells as the cells are transferred from the growth module 604, for example in tubes or vials residing in a reagent cartridge that includes a tube or vial of the cells that have been transferred to the cartridge from the growth module 604. Transformation of the electrocompetent cells can take place in a flow-through electroporation device as described above in relation to FIGS. 4A-4E or in microfuge tubes, test tubes, cuvettes, multi-well plates, microfibers, flow systems, etc. The transformation module 608 preferably allows for temperature control. Control of the transformation module 608 (e.g., addition of reagents, incubation time and temperature) is typically effected by a processor 650, typically a processor that controls all the modules of the multi-module cell processing instrument. It should be noted that instead of or in addition to a transformation module 608, the multi-module cell processing system 600 may comprise a module configured for induction of protein expression and would thus comprise an induction/protein expression module.

The configuration of the transformation module 608 and the preprogrammed transformation reagents and protocols depends on the transformation technique used. Transformation techniques include, but are not limited to, electroporation, lipofection, optoporation, injection, microprecipitation, microinjection, liposomes, particle bombardment, sonoporation, laser-induced poration, bead transfection, calcium phosphate or calcium chloride co-precipitation, DEAE-dextran-mediated transfection, and the like. Additionally, hybrid techniques that exploit the capabilities of both mechanical and chemical transfection methods can be used, e.g., magnetofection. In another example, cationic lipids may be deployed in combination with gene guns or electroporators. Suitable materials and methods for transforming or transfecting target cells can be found, e.g., in Green and Sambrook, *Molecular Cloning: A Laboratory Manual,* 4th ed., Cold Spring Harbor Laboratory Press, Cold Spring Harbor, N.Y., (2014), and other laboratory manuals. After transformation, the cells are allowed to recover, e.g., in a recovery module 610 under optimal temperature and cell media conditions, where the recovery module 610 also typically is under control of a processor 650.

Figure 7:
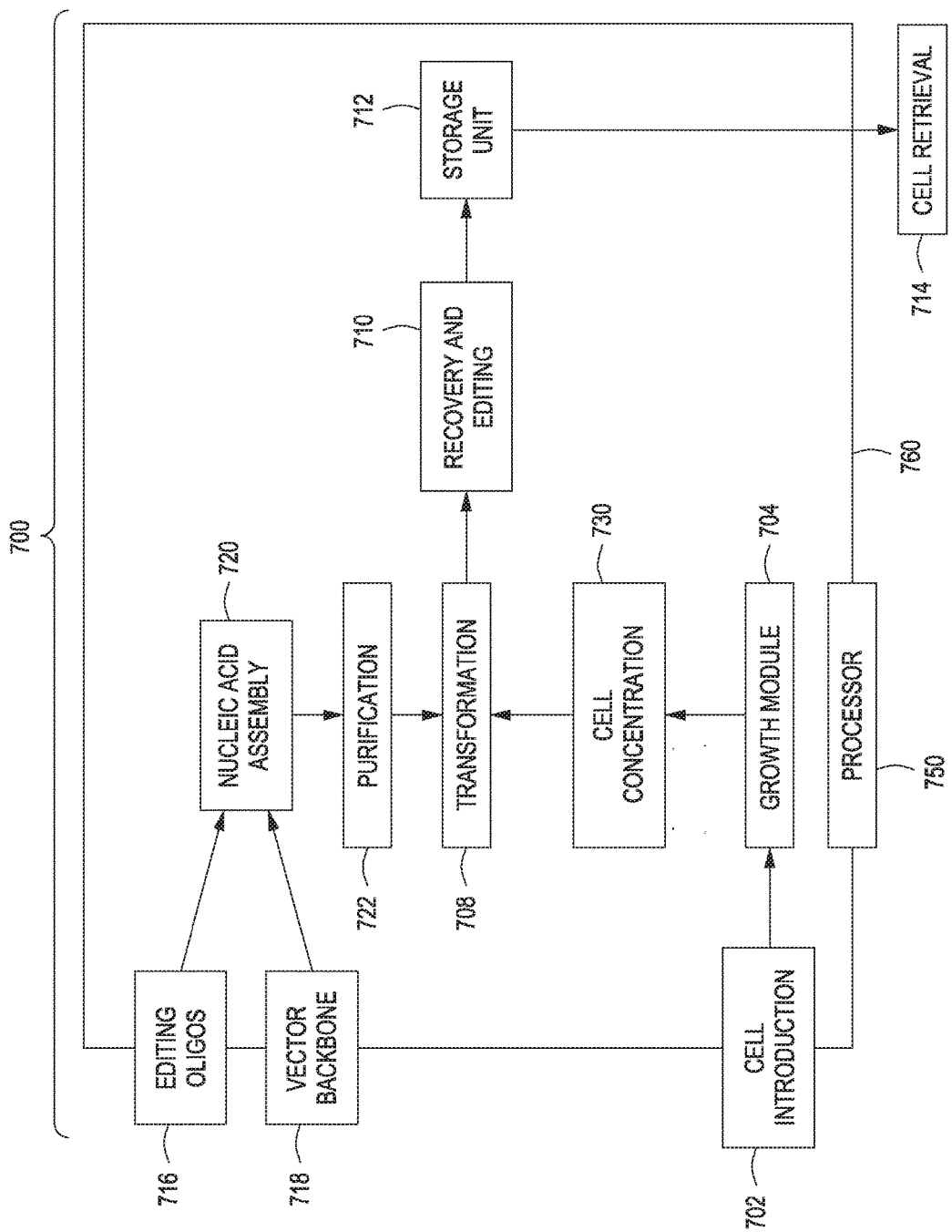
FIG. 7 is a simplified block diagram of yet another embodiment of an exemplary automated multi-module cell processing system that includes a cell growth module.

A second embodiment of a multi-module cell processing system is shown in FIG. 7. As with the embodiment shown in FIG. 6, the cell processing system 700 may include a housing 760, a receptacle for introducing cells to be transformed or transfected 702, and a growth module (a cell growth device) 704. The cells to be transformed are transferred from the cell introduction module 702 to the growth module 704 to be cultured until the cells hit a target OD. Once the cells hit the target OD, the growth module 704 may cool or freeze the cells for later processing or transfer the cells to a concentration module 730 where the cells are rendered electrocompetent and concentrated to a volume optimal for cell transformation as described above in relation to the TFF device. Once concentrated, the cells are then transferred to the transformation module 708.

In addition to the receptacle for receiving cells 702, the multi-module cell processing system 700 may include a receptacle for receiving editing oligonucleotides 716 for, e.g., nucleic acid-guided nuclease editing, and a receptacle for receiving the editing vector backbone 718. Both the editing oligonucleotides and the editing vector backbone are transferred to a nucleic acid assembly module 720, where the editing oligonucleotides are inserted into the editing vector backbone. The assembled nucleic acids may be transferred into an optional purification module 722 for desalting and/or other purification procedures needed to prepare the assembled nucleic acids for transformation. Once the purification processes in the purification module 722 are complete, the assembled nucleic acids are transferred to the transformation module 708, which already contains the cell culture grown to a target OD and that has been rendered electrocompetent. In the transformation module 708, the nucleic acids are introduced into the cells. Following transformation, the cells are transferred into a combined recovery and editing module 710. In some embodiments, the automated multi-module cell processing system 700 is a system that performs gene editing such as an RNA-direct nuclease editing system. For example, see U.S. Ser. No. 16/024,816, filed 30 Jun. 2018; U.S. Ser. No. 16/147,865, filed 30 Sep. 2018; U.S. Ser. No. 16/147,871, filed 30 Sep. 2018; U.S. Ser. No. 16/269,655 filed 7 Feb. 2019; and U.S. Ser. No. 16/269,671, filed 7 Feb. 2019. In the recovery and editing module 710, the cells are allowed to recover post-transformation, and the cells express the editing oligonucleotides which edit desired genes in the cells as described below.

Following editing, the cells are transferred to a storage module 712, where the cells can be stored at, e.g., 4° C. until the cells are retrieved 714 for further study. The multi-module cell processing system 700 is controlled by a processor 750 configured to operate the instrument based on user input. The processor 750 may control the timing, duration, temperature, and other operations of the various modules of the system 700. The processor 750 may be programmed with standard protocol parameters from which a user may select, or a user may specify one or more parameters manually. The processor 750 may control or specify the wavelength at which OD is read in the cell growth module 704, the target OD to which the cells are grown, and the target time at which the cells will reach the target OD. In addition, the processor 750 may notify the user (e.g., via an application to a smart phone or other device) that the cells have reached the target OD as well as update the user as to the progress of the cells in the cell growth module 704 and the other modules in the multi-module cell processing system 700.

Certain embodiments of the multi-module processing system 700 such as the system depicted in FIG. 7 include a nucleic acid assembly module 720 within the system. The nucleic acid assembly module 720 is configured to accept the nucleic acids necessary to facilitate the desired genome editing events, and optionally the appropriate vector backbone for plasmid assembly and subsequent transformation into the cells of interest.

In a nuclease-directed genome editing system, a vector comprises one or more regulatory elements operably linked to a polynucleotide sequence encoding a nucleic acid-guided nuclease and one or more regulatory elements are linked to a guide nucleic acid and a donor DNA comprising the desired edit. Alternatively, the cells may already be expressing the nuclease and the vector may comprise an editing cassette comprising the guide nucleic acid and a donor DNA. Thus, the nucleic acid assembly module 720 in these embodiments is configured to assemble the vector expressing elements contained in an editing cassette. The nucleic acid assembly module 720 may be temperature controlled depending upon the type of nucleic acid assembly used in the instrument. For example, when PCR is utilized in the nucleic acid assembly module 720, the module includes thermocycling capability. When single temperature assembly methods (e.g., isothermal methods) are utilized, the nucleic acid module 720 is configured to have the ability to reach and hold a temperature that optimizes the assembly process being performed. The temperature and duration for maintaining temperatures can be effected by a preprogrammed set of parameters, or manually controlled by the user using the processor unit 750.

Optionally, when a nucleic acid assembly module 720 is included in a multi-module cell processing system 700, the system may also include a purification module 722 to remove unwanted components of the nucleic acid assembly mixture (e.g., salts, minerals) and optionally concentrate the assembled nucleic acids. Examples of methods for exchanging liquid following nucleic acid assembly include magnetic beads (e.g., SPRI or Dynal), silica beads, silica spin columns, glass beads, precipitation (e.g., using ethanol or isopropanol), alkaline lysis, osmotic purification, extraction with butanol, membrane-based separation techniques, filtration etc. In one aspect, the purification module 722 provides filtration, e.g., ultrafiltration. For example, a range of microconcentrators fitted with anisotropic, hydrophilic-generated cellulose membranes of varying porosities may be employed. In another example, purification involves contacting a liquid sample of nucleic acid and an ionic salt with an ion exchanger comprising an insoluble phosphate salt, removing liquid from the nucleic acids in the sample, and eluting said nucleic acid from the ion exchanger.

In one embodiment, the automated multi-module cell processing system 700 is a nuclease-directed genome editing system. Multiple nuclease-based systems exist for providing edits into a cell, and each can be used in either single editing systems such as described above in relation to the automated cell processing system 700 of FIG. 7; sequential editing systems as could be performed in the automated system 700 of FIG. 7 using the modules of the system repeatedly, e.g., using different nuclease-directed systems sequentially to provide two or more genome edits in a cell, and/or utilizing a single nuclease-directed system sequentially to introduce two or more genome edits in a cell. Automated nuclease-directed processing systems can use the nucleases to cleave the cell's genome, to introduce one or more edits into a target region of the cell's genome, or both. Nuclease-directed genome editing mechanisms include zinc-finger editing mechanisms (see Urnov et al., Nature Reviews Genetics, 11:636-64 (2010)), meganuclease editing mechanisms (see Epinat et al., Nucleic Acids Research, 31(11): 2952-62 (2003); and Arnould et al., Journal of Molecular Biology, 371(1):49-65 (2007)), and RNA-guided editing mechanisms (see Jinek et al., Science, 337:816-21 (2012); and Mali et al, Science, 339:823-26 (2013)). In particular embodiments, the nuclease editing system is an inducible system that allows control of the timing of the editing (see Campbell, Biochem J., 473(17): 2573-2589 (2016); and Dow et al., Nature Biotechnology, 33390-94 (2015)). That is, when the cell or population of cells comprising a nucleic acid-guided nuclease encoding DNA is in the presence of the inducer molecule, expression of the nuclease can occur. The ability to modulate nuclease activity can reduce off-target cleavage and facilitate precise genome engineering.

EXAMPLES

Example I: Growth in the Cell Growth Module

One embodiment of the cell growth device as described herein was tested against a conventional cell shaker shaking a 5 ml tube and an orbital shaker shaking a 125 ml baffled flask to evaluate cell growth in bacterial and yeast cells. Additionally, growth of a bacterial cell culture and a yeast cell culture was monitored in real time using an embodiment of the cell growth device described herein.

Figure 8:
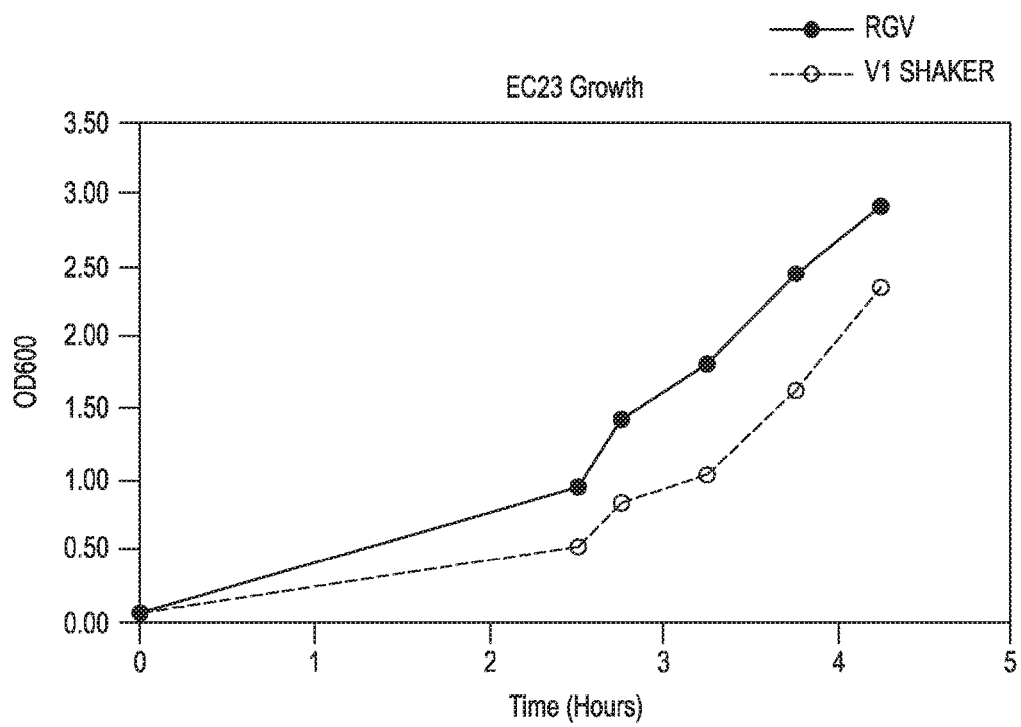
FIG. 8 is a graph demonstrating the effectiveness of a 2-paddle rotating growth vial and cell growth device as described herein for growing an EC23 cell culture vs. a conventional cell shaker.
Figure 9:
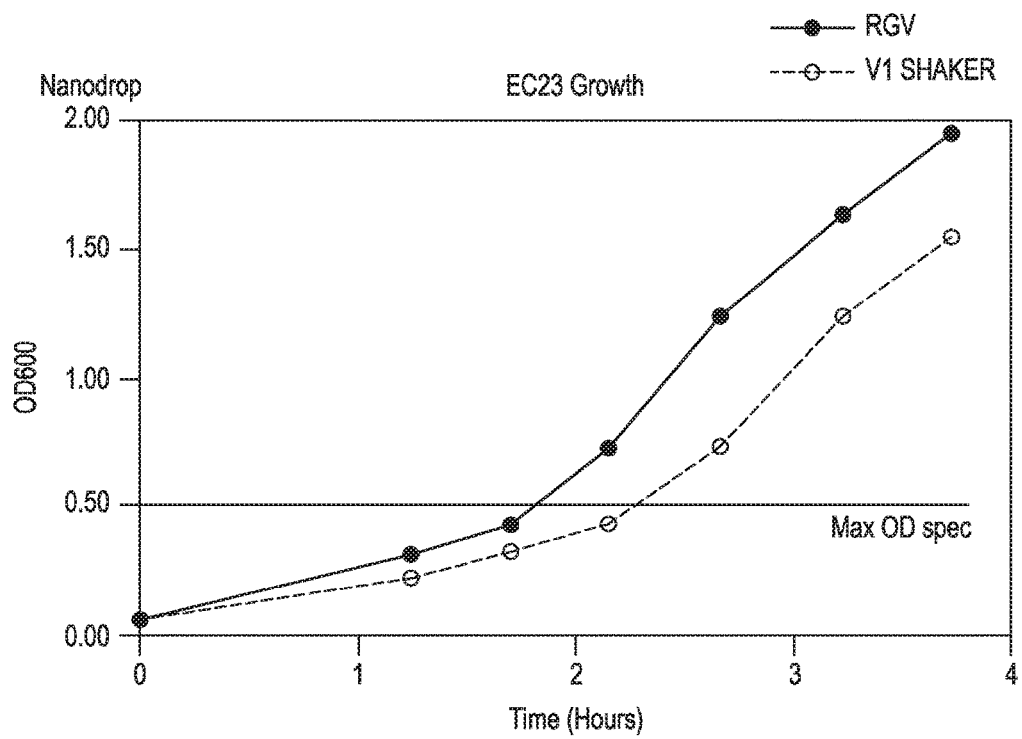
FIG. 9 is a graph demonstrating the effectiveness of a 3-paddle rotating growth vial and cell growth device as described herein for growing an EC23 cell culture vs. a conventional cell shaker.

In a first example, 20 ml EC23 cells (*E. coli* cells) in LB were grown in a 35 ml rotating growth vial with a 2-paddle configuration at 30° C. using the cell growth device as described herein. The rotating growth vial was spun at 600 rpm and oscillated (i.e., the rotation direction was changed) every 1 second. In parallel, 5 ml EC23 cells in LB were grown in a 5 ml tube at 30° C. and were shaken at 750 rpm. $OD_{600}$ was measured at intervals using a NanoDrop™ spectrophotometer (Thermo Fisher Scientific). The results are shown in FIG. 8. The rotating growth vial/cell growth device performed better than the cell shaker in growing the cells to $OD_{600}$ 2.6 in slightly over 4 hours. Another experiment was performed with the same conditions (volumes, cells, oscillation) the only difference being a 3-paddle rotating growth vial was employed with the cell growth device, and the results are shown in FIG. 9. Again, the rotating growth vial/cell growth device performed better than the cell shaker in growing the cells to $OD_{600}$ 1.9.

Figure 10:
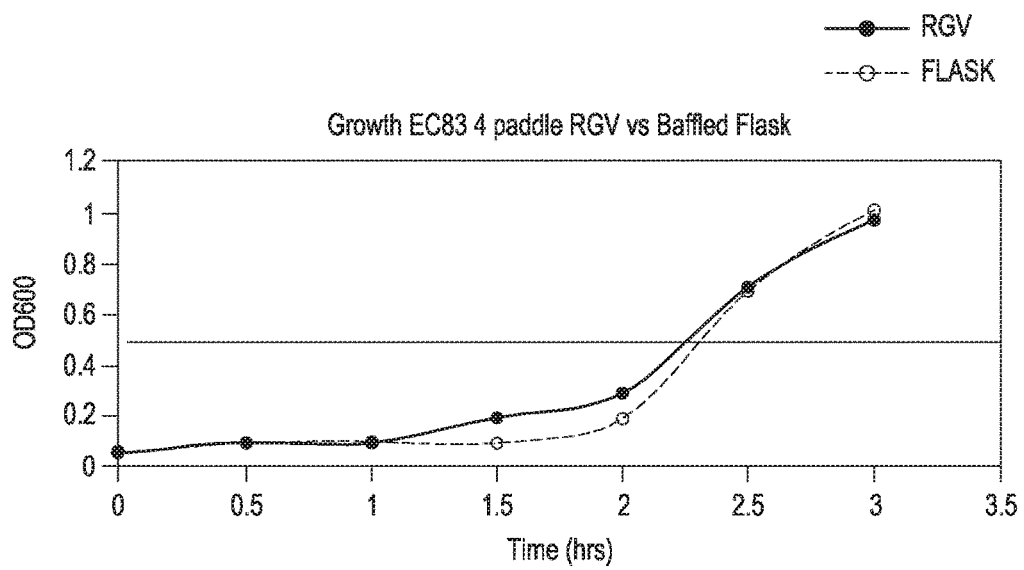
FIG. 10 is a graph demonstrating the effectiveness of a 4-paddle rotating growth vial and cell growth device as described herein for growing an EC138 cell culture vs. a conventional orbital cell shaker.
Figure 11:
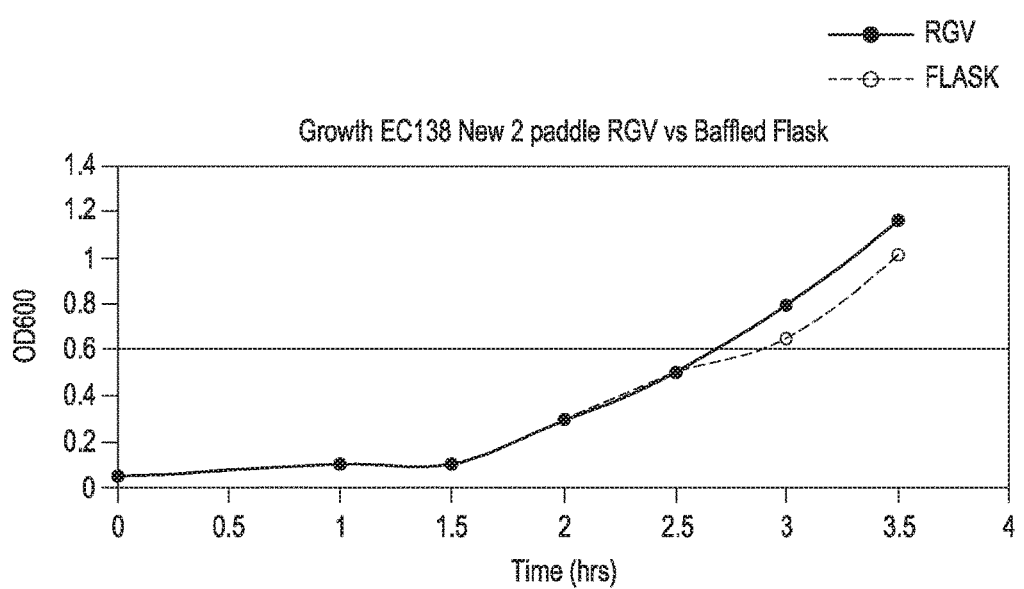
FIG. 11 is a graph demonstrating the effectiveness of a 2-paddle rotating growth vial and cell growth device as described herein for growing an EC138 cell culture vs. a conventional orbital cell shaker.

Two additional experiments were performed, this time comparing the rotating growth vial/cell growth device to a baffled flask and an orbital shaker. In one experiment, 20 ml EC138 cells (*E. coli* cells) in LB were grown in a 35 ml rotating growth vial with a 4-paddle configuration at 30° C. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a NanoDrop™ spectrophotometer (Thermo Fisher Scientific). The results are shown in FIG. 10, demonstrating that the rotating growth vial/cell growth device performed as well as the orbital shaker in growing the cells to $OD_{600}$ 1.0. In a second experiment 20 ml EC138 cells (*E. coli* cells) in LB were grown in a 35 ml rotating growth vial with a 2-paddle configuration at 30° C. using the cell growth device as described herein. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a NanoDrop™ spectrophotometer (Thermo Fisher Scientific). The results are shown in FIG. 11, demonstrating that the rotating growth vial/cell growth device performed as well—or better—as the orbital shaker in growing the cells to $OD_{600}$ 1.2.

Figure 12:
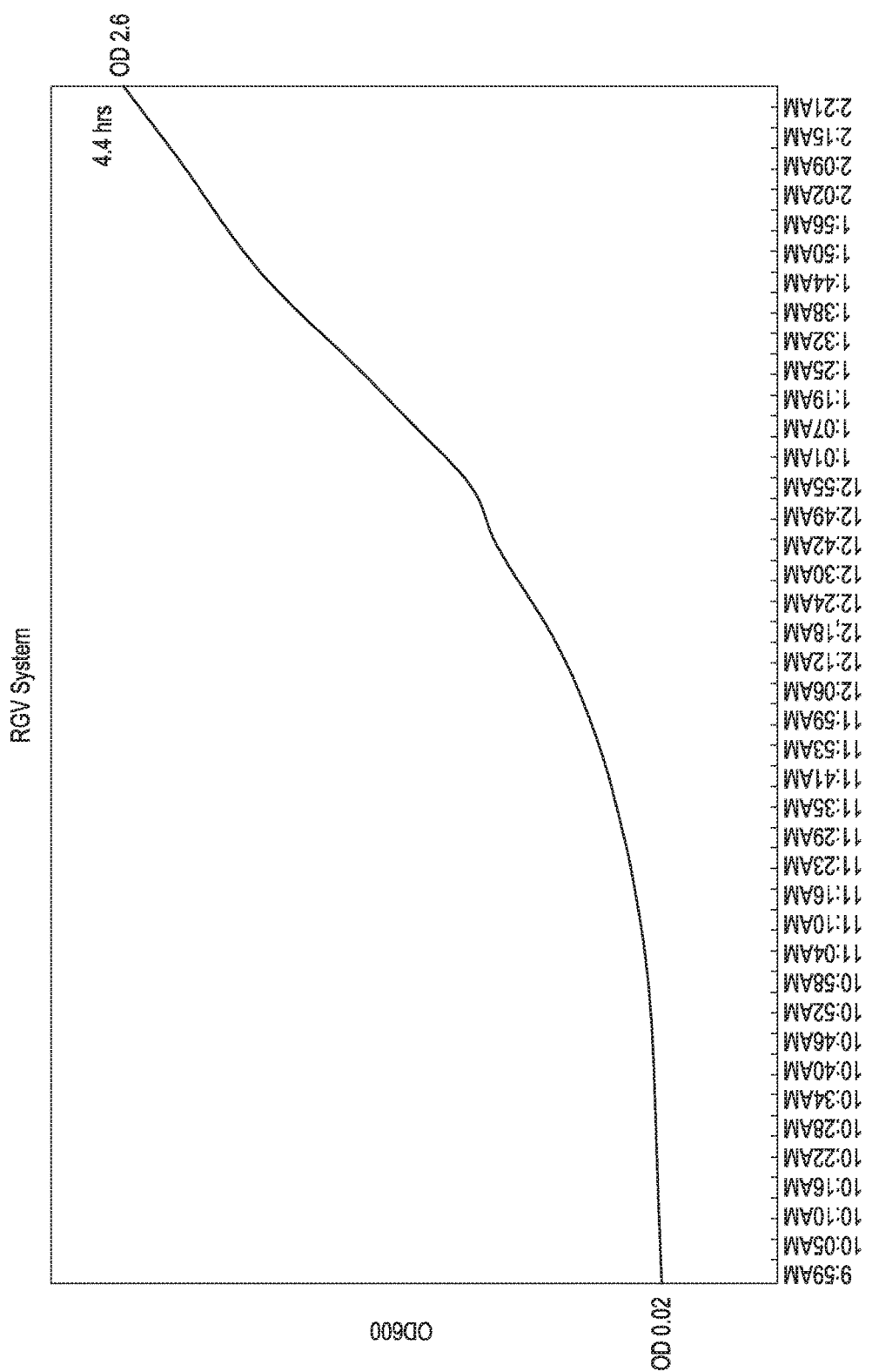
FIG. 12 is a graph demonstrating real-time monitoring of growth of an EC138 cell culture to $OD_{600}$ employing the cell growth device as described herein where a 2-paddle rotating growth vial was used.

In yet another experiment, the rotating growth vial/cell growth device was used to measure $OD_{600}$ in real time. FIG. 12 is a graph showing the results of real time measurement of growth of an EC138 cell culture at 30° C. using oscillating rotation and employing a 2-paddle rotating growth vial. Note that $OD_{600}$ 2.6 was reached in 4.4 hours.

Figure 13:
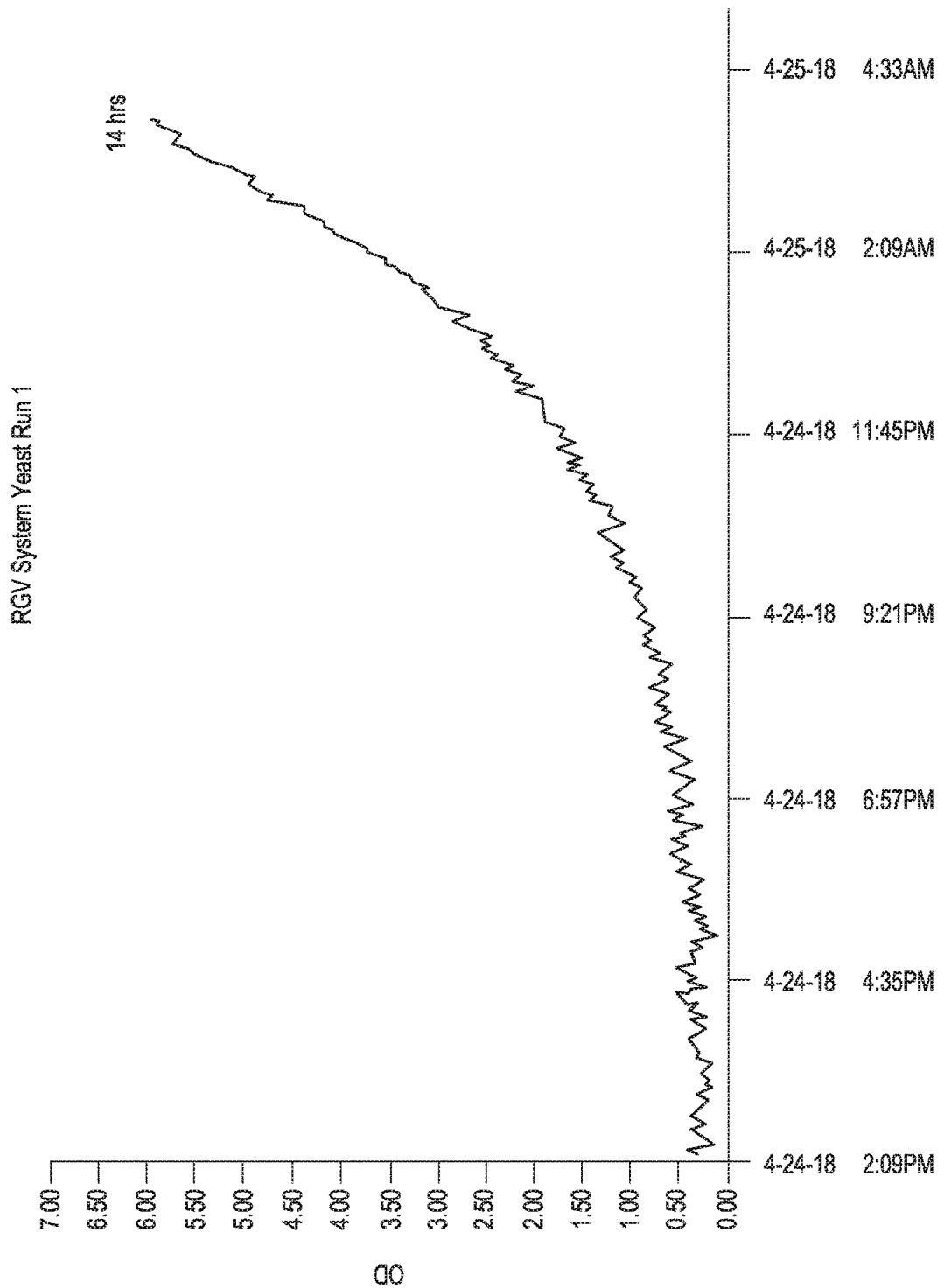
FIG. 13 is a graph demonstrating real-time monitoring of growth of s288c yeast cell culture $OD_{600}$ employing the cell growth device as described herein where a 2-paddle rotating growth vial was used.

In another experiment, the rotating growth vial/cell growth device was used to measure $OD_{600}$ in real time of yeast s288c cells in YPAD. The cells were grown at 30° C. using oscillating rotation and employing a 2-paddle rotating growth vial. FIG. 13 is a graph showing the results. Note that $OD_{600}$ 6.0 was reached in 14 hours.

Example II: Fully-Automated Singleplex RGN-Directed Editing Run

Singleplex automated genomic editing using MAD7 nuclease was successfully performed with an automated multi-module instrument of the disclosure. See U.S. Pat. No. 9,982,279.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent *E. Coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example III: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent *E. Coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to $OD_{600}$ of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. Coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A cell growth device comprising:
a housing;
a motor;
a thermal control device;
a spectrophotometer;
a processor;
an electrical connection configured to be electrically coupled to the thermal control device; and
a rotating growth vial comprising
a vial;
a drive engagement mechanism configured to engage with the motor to spin the vial; and
a light path through the vial for a light beam generated by the spectrophotometer, wherein the spectrophotometer is configured to measure and deliver to the processor an optical density of cells in the vial;
wherein the processor accepts input from a user, receives from the spectrophotometer the optical density of the cells in the vial, and through the electrical connection directs the thermal control device to adjust the temperature of the vial to grow the cells to a target value at a target time; and wherein the processor is programmed to use wavelength values for blanks commensurate with growth medium in the vial.

2. The cell growth device of claim 1, wherein a volume of the cells is from 5-85% of a volume of the rotating growth vial.

3. The cell growth device of claim 1, wherein optical density is measured at a wavelength selected by a user.

4. The cell growth device of claim 1, wherein the optical density is measured continuously.

5. The cell growth device of claim 1, wherein the optical density is measured at intervals specified by the user or programmed into the processor.

6. The cell growth device of claim 1, wherein the vial volume is 1-250 ml.

7. The cell growth device of claim 6, wherein the vial volume is 2-100 ml.

8. The cell growth device of claim 7, wherein the vial volume is 12-35 ml.

9. The cell growth device of claim 1, wherein the vial is fabricated from polycarbonate or polypropylene.

10. The cell growth device of claim 9, wherein the vial is fabricated by injection molding.

11. The cell growth device 1 of claim 1, further comprising a second light path.

12. The cell growth device of claim 1, wherein the rotating growth vial further ecomprises two or more paddles.

13. The cell growth device of claim 12, wherein the rotating growth vial comprises 2-10 paddles.

14. The cell growth device of claim 13, wherein the rotating growth vial comprises 2-6 paddles.

15. The cell growth device of claim 12, wherein the paddles extend from an inner wall of the rotating growth vial toward the interior of the rotating growth vial.

16. The cell growth device of claim 15, wherein the width of the paddles may range from $\frac{1}{20}$ to just under $\frac{1}{2}$ the diameter of the rotating growth vial.

17. The cell growth device of claim 15, wherein the length of the paddles may range from $\frac{4}{5}$ to $\frac{1}{4}$ the length of the main body of the rotating growth vial.

18. The cell growth device of claim 12, wherein the paddles extend from the center of the rotating growth vial toward an inner wall of the rotating growth vial.

19. A cell growth device comprising:
a housing;
a motor;
a thermal control device;
a spectrophotometer;

a processor;

an electrical connection configured to be electrically coupled to the thermal control device; and a disposable rotating cell growth vial comprising a vial; a barcode; a drive engagement mechanism connected to the motor and configured to spin the vial; and a first light path through the vial to measure the optical density of cells in the vial via the spectrophotometer;

wherein the processor accepts input from a user, receives from the spectrophotometer the optical density of the cells, and through the electrical connection directs the thermal device to adjust the temperature of the vial to grow the cells to a target optical density value at a target time, and wherein the processor is programmed to use wavelength values for blanks commensurate with growth medium in the vial.

20. The cell growth device of claim 19, wherein the processor notifies a user when a desired optical density is reached.

* * * * *